US011026964B2

(12) United States Patent
Geall et al.

(10) Patent No.: US 11,026,964 B2
(45) Date of Patent: Jun. 8, 2021

(54) DELIVERY OF RNA TO DIFFERENT CELL TYPES

(71) Applicant: GLAXOSMITHKLINE BIOLOGICALS, SA, Rixensart (BE)

(72) Inventors: Andrew Geall, Littleton, MA (US); Katrin Ramsauer, Vienna (AT); Gillis Otten, Rowley, MA (US); Christian Mandl, Lexington, MA (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/691,042

(22) Filed: Aug. 30, 2017

(65) Prior Publication Data
US 2018/0050059 A1    Feb. 22, 2018

Related U.S. Application Data

(62) Division of application No. 13/808,087, filed as application No. PCT/US2011/043099 on Jun. 7, 2011, now Pat. No. 9,770,463.

(60) Provisional application No. 61/361,780, filed on Jul. 6, 2010.

(51) Int. Cl.
*A61K 31/7088* (2006.01)
*A61K 39/12* (2006.01)
*C12N 15/11* (2006.01)
*A61K 39/155* (2006.01)
*A61K 39/00* (2006.01)

(52) U.S. Cl.
CPC .......... *A61K 31/7088* (2013.01); *A61K 39/12* (2013.01); *A61K 39/155* (2013.01); *C12N 15/111* (2013.01); *A61K 2039/5256* (2013.01); *A61K 2039/53* (2013.01); *A61K 2039/55505* (2013.01); *A61K 2039/55555* (2013.01); *A61K 2039/55566* (2013.01); *C12N 2320/32* (2013.01); *C12N 2760/18534* (2013.01); *C12N 2770/36143* (2013.01)

(58) Field of Classification Search
CPC ................................................ A61K 31/7088
See application file for complete search history.

(56) References Cited

U.S. PATENT DOCUMENTS

| 5,814,482 | A  |   | 9/1998  | Dubensky et al. |
|-----------|----|---|---------|-----------------|
| 6,060,308 | A  | * | 5/2000  | Parrington ........... C07K 14/005 424/186.1 |
| 6,610,321 | B2 | * | 8/2003  | Huang ................. A61K 9/1275 424/450 |
| 6,790,449 | B2 |   | 9/2004  | Collins |
| 9,504,651 | B2 |   | 11/2016 | MacLachlan et al. |
| 9,770,463 | B2 |   | 9/2017  | Geall et al. |
| 2003/0138453 | A1 |   | 7/2003 | O'Hagan et al. |
| 2004/0142025 | A1 |   | 7/2004 | MacLachlan et al. |
| 2005/0064595 | A1 |   | 3/2005 | Maclachlan et al. |
| 2007/0014805 | A1 |   | 1/2007 | Dalencon et al. |
| 2007/0118094 | A1 |   | 5/2007 | Bingham et al. |
| 2008/0057080 | A1 |   | 3/2008 | Luke et al. |
| 2008/0085870 | A1 |   | 4/2008 | Hermanson et al. |
| 2011/0200667 | A1 |   | 8/2011 | Onate Contreras et al. |
| 2016/0024157 | A1 |   | 1/2016 | Masignani et al. |
| 2018/0094033 | A1 |   | 4/2018 | Telford et al. |

FOREIGN PATENT DOCUMENTS

| EP | 3318248 B1      |   | 4/2019  |             |
|----|-----------------|---|---------|-------------|
| EP | 2591103 B1      |   | 8/2019  |             |
| WO | WO93/24640      | * | 12/1993 | ............. C12N 15/85 |
| WO | 1999011808 A1   |   | 3/1999  |             |
| WO | 01/29233 A2     |   | 4/2001  |             |
| WO | 0202606 A2      |   | 1/2002  |             |
| WO | 02/09645 A2     |   | 2/2002  |             |
| WO | 02/06209 A2     |   | 4/2002  |             |
| WO | 0234771 A2      |   | 5/2002  |             |
| WO | 02/061113 A2    |   | 8/2002  |             |
| WO | 02/095023 A2    |   | 11/2002 |             |
| WO | 03018054 A1     |   | 3/2003  |             |
| WO | 2005002619 A2   |   | 1/2005  |             |
| WO | 2005032582 A2   |   | 4/2005  |             |
| WO | 2005111066 A2   |   | 11/2005 |             |
| WO | 2005113782 A1   |   | 12/2005 |             |

(Continued)

OTHER PUBLICATIONS

Fleeton etal (Journal of Infectious Diseases. 2001; 183:1395-1398) (Year: 2001).*
Vasiljeva et al. (Journal of Biological Chemistry. Jun. 9, 2000; 275(23): 17281-17287). (Year: 2000).*
Herweijer et al. (Advanced Drug Delivery Reviews 27 ( 1997) 5-16) (Year: 1997).*
Bramwell (DDT. 2005; 10(22): 1527-1534).
Broz, et al. "Newly described pattern recognition receptors team up against intracellular pathogents", Nat. Rev. Immunol. 13:8: 551-565 (2013).
Buza, J. et al., "CD14+ cells are required for IL-12 response in bovine blood mononuclear cells activated with Toll-like receptor (TLR) 7 and TLR8 ligands", Vet. Immunol. Immunopath. 126(3-4): 273-282 (2008)—XP025676816.

(Continued)

*Primary Examiner* — Scott Long

(57) ABSTRACT

RNA encoding an immunogen is co-delivered to non-immune cells at the site of delivery and also to immune cells which infiltrate the site of delivery. The responses of these two cell types to the same delivered RNA lead to two different effects, which interact to produce a strong immune response against the immunogen. The non-immune cells translate the RNA and express the immunogen. Infiltrating immune cells respond to the RNA by expressing type I interferons and pro-inflammatory cytokines which produce a local adjuvant effect which acts on the immunogen-expressing non-immune cells to upregulate major histocompatibility complex expression, thereby increasing presentation of the translated protein to T cells. The effects on the immune and non-immune cells can be achieved by a single delivery of a single RNA e.g. by a single injection.

18 Claims, 10 Drawing Sheets

(56) References Cited

FOREIGN PATENT DOCUMENTS

| | | | |
|---|---|---|---|
| WO | 2005120152 A2 | 12/2005 | |
| WO | 2005121348 A1 | 12/2005 | |
| WO | 2006078294 A2 | 7/2006 | |
| WO | 2006089264 A2 | 8/2006 | |
| WO | 2006091517 A2 | 8/2006 | |
| WO | 2006092607 A1 | 9/2006 | |
| WO | 2006110413 A2 | 10/2006 | |
| WO | 2006138004 A2 | 12/2006 | |
| WO | 2007047749 A1 | 4/2007 | |
| WO | WO2007/047749 * | 4/2007 | ............ A61K 39/00 |
| WO | 2007049155 A2 | 5/2007 | |
| WO | 2008020330 A2 | 2/2008 | |
| WO | 2009016515 A2 | 2/2009 | |
| WO | 2009031043 A2 | 3/2009 | |
| WO | 2009104092 A2 | 8/2009 | |
| WO | 2009109860 A2 | 9/2009 | |
| WO | 2009132206 A1 | 10/2009 | |
| WO | 2009146867 A1 | 12/2009 | |
| WO | 2010015098 A1 | 2/2010 | |
| WO | 2010059689 A2 | 5/2010 | |
| WO | 2010119343 A2 | 10/2010 | |
| WO | 2011005799 A2 | 1/2011 | |
| WO | 2012006369 A2 | 1/2012 | |
| WO | 2012006372 A1 | 1/2012 | |
| WO | 2012006378 A1 | 1/2012 | |
| WO | 2012006380 A2 | 1/2012 | |
| WO | 2012030901 A1 | 3/2012 | |

OTHER PUBLICATIONS

Carralot, J.P., et al., "Polarization of immunity induced by direct injection of naked sequence-stabilized mRNA vaccines", Cell. Mole. Life Sci. 61(18): 2418-2424 (2004)—XP002355208.
Cheng, W.F., et al, "Enhancement of Sindbis Virus Self-Replicating RNA Vaccine Potency by Linkage of Herpes Simplex Virus Type 1 VP22 Protein to Antigen", J. Viral. 75(5): 2368-2376 (2001)—XP002201711.
Diebold, S.S., et al., "Innate Antiviral Responses by Means of TLR7-Mediated Recognition of Single-Stranded RNA", Science 303(5663): 1529-1531 (2004)—XP002675306.
Fleeton et al (Journal of Infectious Diseases. 2001; 183:1395-1398).
Graham, et al., "Priming Immunization Determines T Helper Cytokine mRNA Expression Patterns in Lungs of Mice Challenged with Respiratory Syncytial Virus." The Journal of Immunology; Aug. 15, 1993; pp. 2032-2040; vol. 151, No. 4.
Greer, C, et al., "A chimeric alphavirus RNA replicon gene-based vaccine for human parainfluenza virus type 3 induces protective immunity against intranasal virus challenge", Vaccine 25(3): 481-489 (2007)—XP005798901.
Hoerr et al (Eur. J. Immunol. 2000; 30:1-7).
Johnson, T, et al., "TLR9 agonist, but not TLR7/8, functions as an adjuvant to diminish FI-RSV vaccine-enhanced disease, while either agonist used as therapy during primary RSV infection increases disease severity", Vaccine 27 (23): 3045-3052 (2009)—XP026058722.
Liljestrom et al. (Journal of Virlology. Aug. 1991; 65(8): 4107-4113).
Martin, et al., "Characterization of formaldehyde-inactivated poliovirus preparations made from live-attenuated strains." Journal of General Virology; 2003; pp. 1781-1788; vol. 84.
Merriam-Webster definition of "virion" (downloaded Mar. 14, 2016).
Saenz-Badillos, et al, "RNA as a tumor vaccine; a review of the literature", Experimental Dermatology; 2001; pp. 143-154; vol. 10, Issue 3.
Sugiyama, T., "Immunoadjuvant effects of polyadenylic:polyuridylic acids through TLR3 and TLR7", Int. Immunolo. 20(1 ): 1-9 (2008)—XP002665154.
W.-Z. Zhou, et al., "RNA Melanoma Vaccine: Induction of Antitumor Immunity by Human Glycoprotein 100 mRNA Immunization." Human Gene Therapy; Nov. 1, 1999; pp. 2719-2724; vol. 10.
Ying, H., et al., "Cancer therapy using self-replicating RNA vaccine", Nat. Med. 5(7):823-827 (1999).
Zhou, X., et al., "Self-replicating Semliki Forest virus RNA as recombinant vaccine", Vaccine 12(16): 1510-1514 (1994).
Rodriguez-Gascon, et al., "Development of nucleic acid vaccines: use of self-amplifying RNA in lipid nanoparticles." International Journal of Nanomedicine; 2014; pp. 1833-1843; vol. 9(1).
Wang, et al., "pH-sensitive immunoliposomes mediate target-cell-specific delivery and controlled expression of a foreign gene in mouse." Proc. Natl. Acad. Sci. USA; 1987; pp. 7851-7855; vol. 84.
Felgner, et al., "Lipofection: A highly efficient, lipid-mediated DNA-transfection procedure." Proc. Natl Acad. Sci. USA; 1987; pp. 7413-7417; vol. 84.
Jeffs et al., "A scalable, extrusion-free method for efficient liposomal encapsulation of plasmid DNA", Pharmaceutical Research, vol. 22, No. 3, Mar. 2005, p. 362-372.
Yoneyama, Fujita, Cytokine & Growth Factor Reviews, (2007), vol. 18, pp. 545-551.
Singh et al., Pharmaceutical Research, (2003), vol. 20, pp. 247-251.
Birdi, K.S., Handbook of Surface and Colloidal Chemistry, CRC Press.
Perri et al., J Virol, (2003), vol. 77, pp. 10394-10403.
O'Hagan et al., J Virology, (2001), vol. 75, pp. 9037-9043.
El Ouahabi et al., Febsletts, (1996), vol. 380, pp. 108-112.
Maurer et al., Biophysical Journal, (2001), vol. 80, pp. 2310-2326.
Giuliani et al., Proc Natl Acad Sci USA, (2006), vol. 103, No. 29, pp. 10834-10839.
Johanning et al., Nucleic Acids Res, (1995), vol. 23, pp. 1495-1501.
Heyes et al., J Controlled Release, (2005), vol. 107, pp. 276-287.
Iavarone et al., Jimmunol, (2011), vol. 186, pp. 4213-422.
Notice of Opposition in relation to European Patent No. 2591103B1 (Appln No. 11736498.4) dated May 27, 2020 (17 pages).
Notice of Opposition in relation to European Patent No. 2591103B1 (Appln No. 11736498.4) dated May 28, 2020 (44 pages).
Malone et al., Proc. Natl. Acad. Sci. USA: Biochemistry, 86:6077-6081 (1989).
Liljestrom et al., Biotechnology, 9:1356-1361 (1991).
Johanning et al., Nucleic Acids Research, 23:1495-1501 (1995).
Kiong et al., Science, 243:1188-1191 (1989).
Lu et al., Cancer Gene Ther., 1(4):245-252 (1994) (abstract).
Certified U.S. Appl. No. 61/265,653, filed Dec. 1, 2009.
Certified U.S. Appl. No. 61/1361,780, filed Jul. 6, 2010.
Leitner et al., Vaccine, 18:765-777 (2000).
Dupuis et al., Cellular Immunology, 186:18-27 (1998).
Dupuis et al., Journal of Immunology, 165:2850-2858 (2000).
Mosca et al., Proc. Natl. Acad. Sci. USA, 105:10501-10506 (2008).
Kumar et al., Biochemical and Biophysical Research Communications, 388:621-625 (2009).
Strejan et al., Journal of Neuroimmunology, 7:27-41 (1984).
Fleeton et al., Journal of Infectious Diseases, 183:1395-1398 (2001).
Vignuzzi et al., Journal of General Virology, 82:1737-1747 (2001).
Cheng et al., Journal of Immunology, 166:6218-6226 (2001).
Saxena et al., Veterinary Microbiology, 136:36-44 (2009).
Jeffs et al., Pharmaceutical Research, 22:362-372 (2005).
Heyes et al., Journal of Controlled Release, 107:276-287 (2005).
Fenske et al., Toxicologic Pathology, 36:21-29 (2008).
Buyens et al., Langmuir, 25:4886-4891 (2009).
Manning et al., Intervirology, 20:164-168 (1983).
Wilson et al., Cell, 17:77-84 (1979).
Zhou et al., Human Gene Therapy, 10:2719-2724 (1999).
Zuckerman, BMJ, 321:1237-1238 (2000).
Certified U.S. Appl. No. 61/1361,794, filed Jul. 6, 2010.
Singh et al., PNAS, 97:811-816 (2000).
Ott et al., Journal of Controlled Release, 79:1-5 (2002).
Bringmann et al., Journal of Biomedicine and Biotechnology, 2010:1-13 (2010).
Zimmermann et al., Nature, 441:111-114 (2006).
Lazzaro et al., Immunology, 146:312-326 (2015).
Anonymous, "Mengovirus", Wikipedia, (Apr. 25, 2020), pp. 1-2, URL: https://en.wikipedia.org/wiki/Mengovirus.
Patentee's Reply to Opposition in relation to European Patent No. 2591103B1 (Appln No. 11736498.4) dated Oct. 23, 2020 (28 pages).

(56) References Cited

OTHER PUBLICATIONS

Johnson signed Declaration dated Oct. 22, 2020 (9 pages).
Crooke Stanley T., Antisense Drug Technology: Principles, Strategies, and Applications, 2nd ed., chapter 9 (2008), pp. 237-270.

* cited by examiner

DELIVERY OF RNA TO DIFFERENT CELL TYPES

This application is a Divisional of application Ser. No. 13/808,087, filed Mar. 27, 2013, which is the U.S. National Phase of International Application No. PCT/US2011/043099, filed Jul. 6, 2011 and published in English, which claims the benefit of U.S. Provisional Application 61/361,780, filed Jul. 6, 2010, the complete contents of which are hereby incorporated herein by reference for all purposes.

TECHNICAL FIELD

This invention is in the field of non-viral delivery of RNA for immunisation.

BACKGROUND ART

The delivery of nucleic acids for immunising animals has been a goal for several years. Various approaches have been tested, including the use of DNA or RNA, of viral or non-viral delivery vehicles (or even no delivery vehicle, in a "naked" vaccine), of replicating or non-replicating vectors, or of viral or non-viral vectors.

There remains a need for further and improved nucleic acid vaccines and, in particular, for improved ways of delivering nucleic acid vaccines.

Disclosure of the Invention

According to the invention, RNA encoding an immunogen is co-delivered to non-immune cells at the site of delivery and also to immune cells (including professional antigen presenting cells) which infiltrate the site of delivery. The non-immune cells (e.g. fibroblasts) respond to the RNA by activating cytoplasmic RNA helicases, leading to a local adjuvant effect. Infiltrating immune cells respond to the RNA by expressing type I interferons (e.g. interferon α and/or β) and pro-inflammatory cytokines (e.g. interleukin 6) and presenting expressed immunogen to T cells. The responses of these two cell types to the same delivered RNA lead to two different effects, which interact to produce a strong immune response against the immunogen, and this result can be achieved by a single delivery of a single RNA e.g. by a single injection.

Thus the invention provides a method of raising an immune response in a vertebrate, comprising administering an immunogen-encoding RNA to a delivery site in a vertebrate and then permitting immune cells to infiltrate the delivery site, such that the RNA separately enters both (a) non-immune cells at the delivery site and (b) the infiltrating immune cells.

The invention also provides an immunogen-encoding RNA for use in an in vivo method of raising an immune response in a vertebrate, wherein the method comprises administering the RNA to a delivery site in the vertebrate and then permitting immune cells to infiltrate the delivery site, such that the RNA separately enters both (a) non-immune cells at the delivery site and (b) the infiltrating immune cells.

The invention also provides the use of an immunogen-encoding RNA in the manufacture medicament for raising an in vivo immune response in a vertebrate, wherein the RNA is prepared for administration to a delivery site in the vertebrate after which immune cells are permitted to infiltrate the delivery site, such that the RNA separately enters both (a) non-immune cells at the delivery site and (b) the infiltrating immune cells.

Administration

The invention involves administration of a RNA molecule to a delivery site in a vertebrate. The delivery site will usually be muscle tissue, such as skeletal muscle. Alternatives to intramuscular administration include, but are not limited to: intradermal, intranasal, intraocular, subcutaneous, intraperitoneal, intravenous, interstitial, buccal, transdermal, or sublingual administration. Intradermal and intramuscular administration are two preferred routes.

Administration can be achieved in various ways. For instance, injection via a needle (e.g. a hypodermic needle) can be used, particularly for intramuscular, subcutaneous, intraocular, intraperitoneal or intravenous administration. Needle-free injection can be used as an alternative.

Intramuscular injection is the preferred way of administering RNA according to the invention. Injection into the upper arm, deltoid or thigh muscle (e.g. anterolateral thigh) is typical.

The delivery site includes non-immune cells, such as muscle cells (which may be multinucleated and may be arranged into fascicles) and/or fibroblasts. RNA enters the cytoplasm of these cells after (or while) being administered to the delivery site. Entry can be via endocytosis e.g. across the sarcolemma of a muscle cell, or across the cell membrane of a fibroblast. After RNA entry (and escape from the endosome), it can bind to RNA helicases such as RIG-I (RLR-1), MDA5 (RLR-2) and/or LGP2 (RLR-3). This binding can initiate RLR-mediated signalling, thereby triggering innate immune pathways which enhance the immunogenic effect of the delivered RNA. Even if the delivered RNA is single-stranded, it can form double-stranded RNA either during replication or due to its secondary structure, which means that the RNA can also initiate PKR-mediated signalling, again leading to the triggering of innate immune pathways. Both RLR-mediated and PKR-mediated signalling can lead to secretion of type I interferons (e.g. interferon α and/or β) by the non-immune cells. The non-immune cells may undergo apoptosis after transfection.

The delivery site also includes immune cells, such as macrophages (e.g. bone marrow derived macrophages), dendritic cells (e.g. bone marrow derived plasmacytoid dendritic cells and/or bone marrow derived myeloid dendritic cells), monocytes (e.g. human peripheral blood monocytes), etc. These immune cells can be present at the delivery site at the time of administration, but will usually infiltrate the delivery site after administration. For example, the tissue damage caused by invasive administration (e.g. caused at the delivery site by a needle) can cause immune cells to infiltrate the damaged area. These infiltrating cells will encounter the RNA which is now at the delivery site and RNA can enter the cytoplasm of these immune cells e.g. via endocytosis. After RNA entry the response of these immune cells includes secretion of type I interferons and/or pro-inflammatory cytokines. The RNA can cause this effect via pattern-recognition receptors, such as toll-like receptors (e.g. TLR7), intracellular helicases (e.g. RIG-I), and PKR (dsRNA-dependent protein kinase). The RNA may or may not be translated by the immune cells, and so the immune cells may or may not express the immunogen. If the immunogen is expressed by the immune cell then it may be presented by the immune cell's MHC-I and/or MHC-II. If the immunogen is not expressed by the immune cell then it may instead be captured by the immune cell from other cells (e.g. non-immune cells) which had taken up RNA and expressed the immunogen, and the immunogen can thus be presented by the immune cell's MHC-II and/or MHC-I. Antigen presentation will generally occur in draining lymph nodes after immune cells have migrated away from the delivery site The infiltration of immune cells at a delivery site can be observed directly e.g. by using labelled immune cells and then either in vivo imaging techniques or biopsy sampling. The ability of RNA to enter the immune cells and the non-immune cells can be detected by sequence-specific detection techniques performed in situ or on an excised sample.

The RNA can be delivered as naked RNA (e.g. merely as an aqueous solution of RNA) but, to enhance both entry to immune and non-immune cells and also subsequent intercellular effects, the RNA is preferably administered in combination with a delivery system, such as a particulate or emulsion delivery system. Three useful delivery systems of interest are (i) liposomes (ii) non-toxic and biodegradable polymer microparticles (iii) cationic submicron oil-in-water emulsions. Liposomes are a preferred delivery system.

Liposomes

Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic and others are cationic. Suitable classes of phospholipid include, but are not limited to, phosphatidylethanolamines, phosphatidylcholines, phosphatidylserines, and phosphatidylglycerols, and some useful phospholipids are listed in Table 1. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC and dodecylphosphocholine. The lipids can be saturated or unsaturated. The use of at least one unsaturated lipid for preparing liposomes is preferred. If an unsaturated lipid has two tails, both tails can be unsaturated, or it can have one saturated tail and one unsaturated tail.

Liposomes can be formed from a single lipid or from a mixture of lipids. A mixture may comprise (i) a mixture of anionic lipids (ii) a mixture of cationic lipids (iii) a mixture of zwitterionic lipids (iv) a mixture of anionic lipids and cationic lipids (v) a mixture of anionic lipids and zwitterionic lipids (vi) a mixture of zwitterionic lipids and cationic lipids or (vii) a mixture of anionic lipids, cationic lipids and zwitterionic lipids. Similarly, a mixture may comprise both saturated and unsaturated lipids. For example, a mixture may comprise DSPC (zwitterionic, saturated), DlinDMA (cationic, unsaturated), and/or DMG (anionic, saturated). Where a mixture of lipids is used, not all of the component lipids in the mixture need to be amphiphilic e.g. one or more amphiphilic lipids can be mixed with cholesterol.

The hydrophilic portion of a lipid can be PEGylated (i.e. modified by covalent attachment of a polyethylene glycol). This modification can increase stability and prevent non-specific adsorption of the liposomes. For instance, lipids can be conjugated to PEG using techniques such as those disclosed in references 1 and 2. Various lengths of PEG can be used e.g. between 0.5-8 kDa.

A mixture of DSPC, DlinDMA, PEG-DMG and cholesterol is used in the examples.

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter ≤50 nm, and LUVs have a diameter >50 nm. Liposomes useful with of the invention are ideally LUVs with a diameter in the range of 50-220 nm. For a composition comprising a population of LUVs with different diameters: (i) at least 80% by number should have diameters in the range of 20-220 nm, (ii) the average diameter (Zav, by intensity) of the population is ideally in the range of 40-200 nm, and/or (iii) the diameters should have a polydispersity index <0.2. The liposome/RNA complexes of reference 17 are expected to have a diameter in the range of 600-800 nm and to have a high polydispersity.

Techniques for preparing suitable liposomes are well known in the art e.g. see references 3 to 5. One useful method is described in reference 6 and involves mixing (i) an ethanolic solution of the lipids (ii) an aqueous solution of the nucleic acid and (iii) buffer, followed by mixing, equilibration, dilution and purification. Preferred liposomes of the invention are obtainable by this mixing process.

RNA is preferably encapsulated within the liposomes, and so the liposome forms a outer layer around an aqueous RNA-containing core. This encapsulation has been found to protect RNA from RNase digestion. The liposomes can include some external RNA (e.g. on the surface of the liposomes), but at least half of the RNA (and ideally all of it) is encapsulated.

Polymeric Microparticles

Various polymers can form microparticles to encapsulate or adsorb RNA. The use of a substantially non-toxic polymer means that a recipient can safely receive the particles, and the use of a biodegradable polymer means that the particles can be metabolised after delivery to avoid long-term persistence. Useful polymers are also sterilisable, to assist in preparing pharmaceutical grade formulations.

Suitable non-toxic and biodegradable polymers include, but are not limited to, poly(a-hydroxy acids), polyhydroxy butyric acids, polylactones (including polycaprolactones), polydioxanones, polyvalerolactone, polyorthoesters, polyanhydrides, polycyanoacrylates, tyrosine-derived polycarbonates, polyvinyl-pyrrolidinones or polyester-amides, and combinations thereof.

In some embodiments, the microparticles are formed from poly(α-hydroxy acids), such as a poly(lactides) ("PLA"), copolymers of lactide and glycolide such as a poly(D,L-lactide-co-glycolide) ("PLG"), and copolymers of D,L-lactide and caprolactone. Useful PLG polymers include those having a lactide/glycolide molar ratio ranging, for example, from 20:80 to 80:20 e.g. 25:75, 40:60, 45:55, 50:50, 55:45, 60:40, 75:25. Useful PLG polymers include those having a molecular weight between, for example, 5,000-200,000 Da e.g. between 10,000-100,000, 20,000-70,000, 30,000-40,000, 40,000-50,000 Da.

The microparticles ideally have a diameter in the range of 0.02 μm to 8 μm. For a composition comprising a population of microparticles with different diameters at least 80% by number should have diameters in the range of 0.03-7 μm.

Techniques for preparing suitable microparticles are well known in the art e.g. see references 5, 7 (in particular chapter 7) and 8. To facilitate adsorption of RNA, a microparticle may include a cationic surfactant and/or lipid e.g. as disclosed in references 9 & 10. An alternative way of making polymeric microparticles is by molding and curing e.g. as disclosed in reference 11.

Microparticles of the invention can have a zeta potential of between 40-100 mV.

One advantage of microparticles over liposomes is that they are readily lyophilised for stable storage. RNA can be adsorbed to the microparticles, and adsorption is facilitated by including cationic materials (e.g. cationic lipids) in the microparticle.

Oil-in-Water Cationic Emulsions

Oil-in-water emulsions are known for adjuvanting influenza vaccines e.g. the MF59™ adjuvant in the FLUAD™ product, and the AS03 adjuvant in the PREPANDRIX™ product. RNA delivery according to the present invention can utilise an oil-in-water emulsion, provided that the emulsion includes one or more cationic molecules. For instance, a cationic lipid can be included in the emulsion to provide a positive droplet surface to which negatively-charged RNA can attach.

The emulsion comprises one or more oils. Suitable oil(s) include those from, for example, an animal (such as fish) or a vegetable source. The oil is ideally biodegradable (metabolisable) and biocompatible. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Preferred emulsions comprise squalene, a shark liver oil which is a branched, unsaturated terpenoid ($C_{30}H_{50}$; $RCH_3)_2C[=CH-CH_2CH_2C(CH_3)]_2=CHCH_2-_2$; 2,6,10,15,19,23-hexamethyl-2,6,10,14,18,22-tetracosahexaene; CAS RN 7683-64-9). Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α, β, γ, δ, ε or ξ or tocopherols can be used, but αa-tocopherols are preferred. D-α-tocopherol and DL-α-tocopherol can both be used. A preferred α-tocopherol is DL-α-tocopherol. An oil combination comprising squalene and a tocopherol (e.g. DL-α-tocopherol) can be used.

The oil in the emulsion may comprise a combination of oils e.g. squalene and at least one further oil.

The aqueous component of the emulsion can be plain water (e.g. w.f.i.) or can include further components e.g. solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. A buffered aqueous phase is preferred, and buffers will typically be included in the 5-20 mM range.

The emulsion also includes a cationic lipid. Preferably this lipid is a surfactant so that it can facilitate formation and stabilisation of the emulsion. Useful cationic lipids generally contains a nitrogen atom that is positively charged under physiological conditions e.g. as a tertiary or quaternary amine. This nitrogen can be in the hydrophilic head group of an amphiphilic surfactant. Useful cationic lipids include, but are not limited to: 1,2-dioleoyloxy-3-(trimethylammonio) propane (DOTAP), 3'-[N-(N',N'-Dimethylaminoethane)-carbamoyl]Cholesterol (DC Cholesterol), dimethyldioctadecyl-ammonium (DDA e.g. the bromide), 1,2-Dimyristoyl-3-Trimethyl-AmmoniumPropane (DMTAP), dipalmitoyl (C16:0)trimethyl ammonium propane (DPTAP), distearoyltrimethylammonium propane (DSTAP). Other useful cationic lipids are: benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC), cetyl trimethylammonium chloride (CTAC), N,N',N'-polyoxyethylene (10)-N-tallow-1,3-diaminopropane, dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl[-benzenemetha-naminium chloride (DEBDA), dialkyldimetylammonium salts, [1-(2,3-dioleyloxy)-propyl]-N,N,N, trimethylammonium chloride, 1,2-diacyl-3-(trimethylammonio) propane (acyl group=dimyristoyl, dipalmitoyl, distearoyl, dioleoyl), 1,2-diacyl-3 (dimethyl-ammonio)propane (acyl group=dimyristoyl, dipalmitoyl, distearoyl, dioleoyl), 1,2-dioleoyl-3-(4'-trimethyl-ammonio) butanoyl-sn-glycerol, 1,2-dioleoyl 3-succinyl-sn-glycerol choline ester, cholesteryl (4'-trimethylammonio) butanoate, N-alkyl pyridinium salts (e.g. cetylpyridinium bromide and cetylpyridinium chloride), N-alkylpiperidinium salts, dicationic bolaform electrolytes ($C_{12}Me_6$; $C_{12}Bu_6$), dialkylglycetylphosphorylcholine, lysolecithin, L-α dioleoyl-phosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group ($C_{12}GluPhC_nN^+$), ditetradecyl glutamate ester with pendant amino group ($C_{12}GluPhC_nN^+$), cationic derivatives of cholesterol, including but not limited to cholesteryl-3 β-oxysuccinamidoethylenetrimethylammonium salt, cholesteryl-3 β-oxysuccinamidoethylene-dimethylamine, cholesteryl-3 β-carboxyamidoethylenetrimethylammonium salt, and cholesteryl-3 β-carboxyamidoethylenedimethylamine. Other useful cationic lipids are described in refs. 12 & 13.

The cationic lipid is preferably biodegradable (metabolisable) and biocompatible.

In addition to the oil and cationic lipid, an emulsion can include a non-ionic surfactant and/or a zwitterionic surfactant. Such surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IG-EPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the Spans), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin and Triton X-100.

Mixtures of these surfactants can be included in the emulsion e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxy-polyethoxyethanol (Triton X-100) is also suitable. Another useful combination comprises laureth 9 plus a polyoxyethylene sorbitan ester and/or an octoxynol. Useful mixtures can comprise a surfactant with a HLB value in the range of 10-20 (e.g. polysorbate 80, with a HLB of 15.0) and a surfactant with a HLB value in the range of 1-10 (e.g. sorbitan trioleate, with a HLB of 1.8).

Preferred amounts of oil (% by volume) in the final emulsion are between 2-20% e.g. 5-15%, 6-14%, 7-13%, 8-12%. A squalene content of about 4-6% or about 9-11% is particularly useful.

Preferred amounts of surfactants (% by weight) in the final emulsion are between 0.001% and 8%. For example: polyoxyethylene sorbitan esters (such as polysorbate 80) 0.2 to 4%, in particular between 0.4-0.6%, between 0.45-0.55%, about 0.5% or between 1.5-2%, between 1.8-2.2%, between 1.9-2.1%, about 2%, or 0.85-0.95%, or about 1%; sorbitan esters (such as sorbitan trioleate) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth 9) 0.1 to 8%, preferably 0.1 to 10% and in particular 0.1 to 1% or about 0.5%.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (excess oil).

An important parameter for ensuring immunostimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 250 nm e.g. less than 200 nm, less than 150 nm. The average droplet size is usefully in the range of 80-180 nm. Ideally, at least 80% (by number) of the emulsion's oil droplets are less than 250 nm in diameter, and preferably at least 90%. Apparatuses for determining the average droplet size in an emulsion, and the size distribution, are commercially available. These these typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan).

Ideally, the distribution of droplet sizes (by number) has only one maximum i.e. there is a single population of droplets distributed around an average (mode), rather than having two maxima. Preferred emulsions have a polydispersity of <0.4 e.g. 0.3, 0.2, or less.

Suitable emulsions with submicron droplets and a narrow size distribution can be obtained by the use of microfluidisation. This technique reduces average oil droplet size by propelling streams of input components through geometrically fixed channels at high pressure and high velocity. These streams contact channel walls, chamber walls and each other. The results shear, impact and cavitation forces cause a reduction in droplet size. Repeated steps of microfluidisation can be performed until an emulsion with a desired droplet size average and distribution are achieved.

As an alternative to microfluidisation, thermal methods can be used to cause phase inversion, as disclosed in reference 14. These methods can also provide a submicron emulsion with a tight particle size distribution.

Preferred emulsions can be filter sterilised i.e. their droplets can pass through a 220 nm filter. As well as providing a sterilisation, this procedure also removes any large droplets in the emulsion.

In certain embodiments, the cationic lipid in the emulsion is DOTAP. The cationic oil-in-water emulsion may comprise from about 0.5 mg/ml to about 25 mg/ml DOTAP. For example, the cationic oil-in-water emulsion may comprise DOTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 12 mg/ml, about 18 mg/ml, about 20 mg/ml, about 21.8 mg/ml, about 24 mg/ml, etc. In an exemplary embodiment, the cationic oil-in-water emulsion comprises from about 0.8 mg/ml to about 1.6 mg/ml DOTAP, such as 0.8 mg/ml, 1.2 mg/ml, 1.4 mg/ml or 1.6 mg/ml.

In certain embodiments, the cationic lipid is DC Cholesterol. The cationic oil-in-water emulsion may comprise DC Cholesterol at from about 0.1 mg/ml to about 5 mg/ml DC Cholesterol. For example, the cationic oil-in-water emulsion may comprise DC Cholesterol from about 0.1 mg/ml to about 5 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.62 mg/ml to about 5 mg/ml, from about 1 mg/ml to about 5 mg/ml, from about 1.5 mg/ml to about 5 mg/ml, from about 2 mg/ml to about 5 mg/ml, from about 2.46 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, from about 0.1 mg/ml to about 4.92 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.46 mg/ml, from about 0.1 mg/ml to about 2 mg/ml, from about 0.1 mg/ml to about 1.5 mg/ml, from about 0.1 mg/ml to about 1 mg/ml, from about 0.1 mg/ml to about 0.62 mg/ml, about 0.15 mg/ml, about 0.3 mg/ml, about 0.6 mg/ml, about 0.62 mg/ml, about 0.9 mg/ml, about 1.2 mg/ml, about 2.46 mg/ml, about 4.92 mg/ml, etc. In an exemplary embodiment, the cationic oil-in-water emulsion comprises from about 0.62 mg/ml to about 4.92 mg/ml DC Cholesterol, such as 2.46 mg/ml.

In certain embodiments, the cationic lipid is DDA. The cationic oil-in-water emulsion may comprise from about 0.1 mg/ml to about 5 mg/ml DDA. For example, the cationic oil-in-water emulsion may comprise DDA at from about 0.1 mg/ml to about 5 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.5 mg/ml, from about 0.1 mg/ml to about 2 mg/ml, from about 0.1 mg/ml to about 1.5 mg/ml, from about 0.1 mg/ml to about 1.45 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.6 mg/ml to about 5 mg/ml, from about 0.73 mg/ml to about 5 mg/ml, from about 0.8 mg/ml to about 5 mg/ml, from about 0.9 mg/ml to about 5 mg/ml, from about 1.0 mg/ml to about 5 mg/ml, from about 1.2 mg/ml to about 5 mg/ml, from about 1.45 mg/ml to about 5 mg/ml, from about 2 mg/ml to about 5 mg/ml, from about 2.5 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, about 1.2 mg/ml, about 1.45 mg/ml, etc. Alternatively, the cationic oil-in-water emulsion may comprise DDA at about 20 mg/ml, about 21 mg/ml, about 21.5 mg/ml, about 21.6 mg/ml, about 25 mg/ml. In an exemplary embodiment, the cationic oil-in-water emulsion comprises from about 0.73 mg/ml to about 1.45 mg/ml DDA, such as 1.45 mg/ml.

Certain preferred compositions of the invention for administration to a patient comprise squalene, span 85, polysorbate 80, and DOTAP. For instance: squalene may be present at 5-15 mg/ml; span 85 may be present at 0.5-2 mg/ml; polysorbate 80 may be present at 0.5-2 mg/l; and DOTAP may be present at 0.1-10 mg/ml. The emulsion can include the same amount (by volume) of span 85 and polysorbate 80. The emulsion can include more squalene than surfactant. The emulsion can include more squalene than DOTAP.

The RNA

The invention involves in vivo delivery of RNA which encodes an immunogen. The RNA is translated by non-immune cells at the delivery site, leading to expression of the immunogen, and it also causes immune cells to secrete type I interferons and/or pro-inflammatory cytokines which provide a local adjuvant effect. The non-immune cells may also secrete type I interferons and/or pro-inflammatory cytokines in response to the RNA.

The RNA is +-stranded, and so it can be translated by the non-immune cells without needing any intervening replication steps such as reverse transcription. It can also bind to TLR7 receptors expressed by immune cells, thereby initiating an adjuvant effect.

Preferred +-stranded RNAs are self-replicating. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall results of this sequence of transcriptions is a huge amplification in the number of the introduced replicon RNAs and so the encoded immunogen becomes a major polypeptide product of the cells.

As shown below, a self-replicating activity is not required for a RNA to provide an adjuvant effect, although it can enhance post-transfection secretion of cytokines. The self-replicating activity is particularly useful for achieving high level expression of the immunogen by non-immune cells. It can also enhance apoptosis of the non-immune cells.

One suitable system for achieving self-replication is to use an alphavirus-based RNA replicon. These +-stranded replicons are translated after delivery to a cell to give of a replicase (or replicase-transcriptase). The replicase is translated as a polyprotein which auto-cleaves to provide a replication complex which creates genomic −-strand copies of the +-strand delivered RNA. These −-strand transcripts can themselves be transcribed to give further copies of the +-stranded parent RNA and also to give a subgenomic transcript which encodes the immunogen. Translation of the subgenomic transcript thus leads to in situ expression of the immunogen by the infected cell. Suitable alphavirus replicons can use a replicase from a sindbis virus, a semliki forest virus, an eastern equine encephalitis virus, a venezuelan equine encephalitis virus, etc. Mutant or wild-type virus sequences can be used e.g. the attenuated TC83 mutant of VEEV has been used in replicons [15].

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non-structural replicase polyprotein, it is preferred that a self-replicating RNA molecule of the invention does not encode alphavirus structural proteins. Thus a preferred self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5) open reading frame encodes a replicase; the second (3) open reading frame encodes an immunogen. In some embodiments the RNA may have additional (e.g. downstream) open reading frames e.g. to encode further immunogens (see below) or to encode accessory polypeptides.

A self-replicating RNA molecule can have a 5' sequence which is compatible with the encoded replicase.

Self-replicating RNA molecules can have various lengths but they are typically 5000-25000 nucleotides long e.g. 8000-15000 nucleotides, or 9000-12000 nucleotides. Thus the RNA is longer than seen in siRNA delivery.

A RNA molecule useful with the invention may have a 5' cap (e.g. a 7-methylguanosine). This cap can enhance in vivo translation of the RNA.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding and thus promote adjuvant effects.

A RNA molecule may have a 3' poly-A tail. It may also include a poly-A polymerase recognition sequence (e.g. AAUAAA) near its 3' end.

A RNA molecule useful with the invention will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

A RNA molecule useful with the invention can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

As discussed in reference 16, the self-replicating RNA can include (in addition to any 5' cap structure) one or more nucleotides having a modified nucleobase. Thus the RNA can comprise m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2'-O-methyladenosine); ms2m6A (2-methylthio-N6-methyladenosine); i6A (N6-isopentenyladenosine); ms2i6A (2-methylthio-N6isopent- enyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6.-hydroxynorvalyl-carbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6, N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine);

imG2 (isoguanosine); or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, or an abasic nucleotide. For instance, a self-replicating RNA can include one or more modified pyrimidine nucleobases, such as pseudouridine and/or 5-methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7'-methylguanosine). In other embodiments, the RNA may include a 5' cap comprising a 7'-methylguanosine, and the first 1, 2 or 3 5' ribonucleotides may be methylated at the 2' position of the ribose.

A RNA used with the invention ideally includes only phosphodiester linkages between nucleosides, but in some embodiments it can contain phosphoramidate, phosphorothioate, and/or methylphosphonate linkages.

Ideally, administered RNA includes fewer than 10 different species of RNA e.g. 5, 4, 3, or 2 different species; most preferably, a composition includes a single RNA species i.e. all RNA molecules in the composition (e.g. within a liposome) have the same sequence and same length.

The Immunogen

RNA molecules used with the invention encode a polypeptide immunogen. After administration of the RNA the immunogen is translated in vivo and can elicit an immune response in the recipient. The immunogen may elicit an immune response against a bacterium, a virus, a fungus or a parasite (or, in some embodiments, against an allergen; and in other embodiments, against a tumor antigen). The immune response may comprise an antibody response (usually including IgG) and/or a cell-mediated immune response. The polypeptide immunogen will typically elicit an immune response which recognises the corresponding bacterial, viral, fungal or parasite (or allergen or tumour) polypeptide, but in some embodiments the polypeptide may act as a mimotope to elicit an immune response which recognises a bacterial, viral, fungal or parasite saccharide. The immunogen will typically be a surface polypeptide e.g. an adhesin, a hemagglutinin, an envelope glycoprotein, a spike glycoprotein, etc.

RNA molecules can encode a single polypeptide immunogen or multiple polypeptides. Multiple immunogens can be presented as a single polypeptide immunogen (fusion polypeptide) or as separate polypeptides. If immunogens are expressed as separate polypeptides then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

Unlike references 17 and 18, the RNA encodes an immunogen. For the avoidance of doubt, the invention does not encompass RNA which encodes a firefly luciferase or which encodes a fusion protein of E. coli β-galactosidase or which encodes a green fluorescent protein (GFP). Also, the RNA is not total mouse thymus RNA.

In some embodiments the immunogen elicits an immune response against one of these bacteria:
  Neisseria meningitidis: useful immunogens include, but are not limited to, membrane proteins such as adhesins, autotransporters, toxins, iron acquisition proteins, and factor H binding protein. A combination of three useful polypeptides is disclosed in reference 19.
  Streptococcus pneumoniae: useful polypeptide immunogens are disclosed in reference 20. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.
  Streptococcus pyogenes: useful immunogens include, but are not limited to, the polypeptides disclosed in references 21 and 22.
  Moraxella catarrhalis.
  Bordetella pertussis: Useful pertussis immunogens include, but are not limited to, pertussis toxin or toxoid (PT), filamentous haemagglutinin (FHA), pertactin, and agglutinogens 2 and 3.
  Staphylococcus aureus: Useful immunogens include, but are not limited to, the polypeptides disclosed in reference 23, such as a hemolysin, esxA, esxB, ferrichrome-binding protein (sta006) and/or the sta011 lipoprotein.
  Clostridium tetani: the typical immunogen is tetanus toxoid.
  Cornynebacterium diphtheriae: the typical immunogen is diphtheria toxoid.
  Haemophilus influenzae: Useful immunogens include, but are not limited to, the polypeptides disclosed in references 24 and 25.
  Pseudomonas aeruginosa
  Streptococcus agalactiae: useful immunogens include, but are not limited to, the polypeptides disclosed in reference 21.
  Chlamydia trachomatis: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in reference 26. LcrE [27] and HtrA [28] are two preferred immunogens.
  Chlamydia pneumoniae: Useful immunogens include, but are not limited to, the polypeptides disclosed in reference 29.
  Helicobacter pylori: Useful immunogens include, but are not limited to, CagA, VacA, NAP, and/or urease [30].
  Escherichia coli: Useful immunogens include, but are not limited to, immunogens derived from enterotoxigenic E. coli (ETEC), enteroaggregative E. coli (EAggEC), diffusely adhering E. coli (DAEC), enteropathogenic E. coli (EPEC), extraintestinal pathogenic E. coli (ExPEC) and/or enterohemorrhagic E. coli (EHEC). ExPEC strains include uropathogenic E. coli (UPEC) and meningitis/sepsis-associated E. coli (MNEC). Useful UPEC polypeptide immunogens are disclosed in references 31 and 32. Useful MNEC immunogens are disclosed in reference 33. A useful immunogen for several E. coli types is AcfD [34].

*Bacillus anthracis*
*Yersinia pestis*: Useful immunogens include, but are not limited to, those disclosed in references 35 and 36.
*Staphylococcus epidermis*

*Clostridium perfringens* or *Clostridium botulinums*

*Legionella pneumophila*

*Coxiella burnetii*

*Brucella*, such as *B. abortus, B. canis, B. melitensis, B. neotomae, B. ovis, B. suis, B. pinnipediae.*

*Francisella*, such as *F. novicida, F. philomiragia, F. tularensis.*

*Neisseria gonorrhoeae*

*Treponema pallidum*

*Haemophilus ducreyi*

*Enterococcus faecalis* or *Enterococcus faecium*

*Staphylococcus saprophyticus*

*Yersinia enterocolitica*

*Mycobacterium tuberculosis*

*Rickettsia*

*Listeria monocytogenes*

*Vibrio cholerae*

*Salmonella typhi*

*Borrelia burgdorferi*

*Porphyromonas gingivalis*

*Klebsiella*

In some embodiments the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: Viral immunogens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles).

Poxviridae: Viral immunogens include, but are not limited to, those derived from Orthopoxvirus such as Variola vera, including but not limited to, Variola major and Variola minor.

Picornavirus: Viral immunogens include, but are not limited to, those derived from Picornaviruses, such as Enteroviruses, Rhinoviruses, Heparnavirus, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: Viral immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Heparnavirus: Viral immunogens include, but are not limited to, those derived from a Heparnavirus, such as hepatitis A virus (HAV).

Filovirus: Viral immunogens include, but are not limited to, those derived from a filovirus, such as an Ebola virus (including a Zaire, Ivory Coast, Reston or Sudan ebolavirus) or a Marburg virus.

Togavirus: Viral immunogens include, but are not limited to, those derived from a Togavirus, such as a Rubivirus, an Alphavirus, or an Arterivirus. This includes rubella virus.

Flavivirus: Viral immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: Viral immunogens include, but are not limited to, those derived from a Pestivirus, such as Bovine viral diarrhea (BVDV), Classical swine fever (CSFV) or Border disease (BDV).

Hepadnavirus: Viral immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: Viral immunogens include, but are not limited to, those derived from a Rhabdovirus, such as a Lyssavirus (e.g. a Rabies virus) and Vesiculovirus (VSV).

Caliciviridae: Viral immunogens include, but are not limited to, those derived from Calciviridae, such as Norwalk virus (Norovirus), and Norwalk-like Viruses, such as Hawaii Virus and Snow Mountain Virus.

Coronavirus: Viral immunogens include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Retrovirus: Viral immunogens include, but are not limited to, those derived from an Oncovirus, a Lentivirus (e.g. HIV-1 or HIV-2) or a Spumavirus.

Reovirus: Viral immunogens include, but are not limited to, those derived from an Orthoreovirus, a Rotavirus, an Orbivirus, or a Coltivirus.

Parvovirus: Viral immunogens include, but are not limited to, those derived from Parvovirus B19.

Herpesvirus: Viral immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: Viral immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: Viral immunogens include those derived from adenovirus serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. album, var. discoides, var. ochraceum, *Trichophyton violaceum,* and/or *Trichophyton faviforme;* or from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi;* the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiospermum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In some embodiments the immunogen elicits an immune response against a parasite from the *Plasmodium* genus, such as *P. falciparum, P. vivax, P. malariae* or *P. ovale.* Thus the invention may be used for immunising against malaria. In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi.*

In some embodiments the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale,* and *Sorghum,* the orders of Asterales and Urticales including herbs of the genera *Ambrosia, Artemisia,* and *Parietaria.* Other important inhalation allergens are those from house dust mites of the genus *Dermatophagoides* and *Euroglyphus,* storage mite e.g. *Lepidoglyphys, Glycyphagus* and *Tyrophagus,* those from cockroaches, midges and fleas e.g. *Blatella, Periplaneta, Chironomus* and *Ctenocepphalides,* and those from mammals such as cat, dog and horse, venom allergens including such originating from stinging or biting insects such as those from the taxonomic order of Hymenoptera including bees (*Apidae*), wasps (*Vespidea*), and ants (*Formicoidae*).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, pl85erbB2, pl80erbB-3, c-met, mn-23H1, TAG-72-4, CA19-9, CA72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

Pharmaceutical Compositions

RNA will be administered as a component in a pharmaceutical composition for immunising subjects against various diseases. These compositions will typically include a pharmaceutically acceptable carrier in addition to the RNA, often as part of a delivery system as described above. A thorough discussion of pharmaceutically acceptable carriers is available in reference 37.

A pharmaceutical composition of the invention may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da. Where a RNA is encapsulated, in some embodiments such agonist(s) are also encapsulated with the RNA, but in other embodiments they are unencapsulated. Where a RNA is adsorbed to a particle, in some embodiments such agonist(s) are also adsorbed with the RNA, but in other embodiments they are unadsorbed.

Pharmaceutical compositions of the invention may include the particles in plain water (e.g. w.f.i.) or in a buffer e.g. a phosphate buffer, a Tris buffer, a borate buffer, a succinate buffer, a histidine buffer, or a citrate buffer. Buffer salts will typically be included in the 5-20 mM range.

Pharmaceutical compositions of the invention may have a pH between 5.0 and 9.5 e.g. between 6.0 and 8.0.

Compositions of the invention may include sodium salts (e.g. sodium chloride) to give tonicity. A concentration of 10±2 mg/ml NaCl is typical e.g. about 9 mg/ml.

Compositions of the invention may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 μM e.g. 0.1 mM. A citrate salt, such as sodium citrate, can also act as a chelator, while advantageously also providing buffering activity.

Pharmaceutical compositions of the invention may have an osmolality of between 200 mOsm/kg and 400 mOsm/kg, e.g. between 240-360 mOsm/kg, or between 290-310 mOsm/kg.

Pharmaceutical compositions of the invention may include one or more preservatives, such as thiomersal or 2-phenoxyethanol. Mercury-free compositions are preferred, and preservative-free vaccines can be prepared.

Pharmaceutical compositions of the invention are preferably sterile.

Pharmaceutical compositions of the invention are preferably non-pyrogenic e.g. containing <1 EU (endotoxin unit, a standard measure) per dose, and preferably <0.1 EU per dose.

Pharmaceutical compositions of the invention are preferably gluten free.

Pharmaceutical compositions of the invention may be prepared in unit dose form. In some embodiments a unit dose may have a volume of between 0.1-1.0 ml e.g. about 0.5 ml.

The compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are typical.

Compositions comprise an immunologically effective amount of RNA, as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The RNA content of compositions of the invention will generally be expressed in terms of the amount of RNA per dose. A preferred dose has ≤10 μg RNA, and expression can be seen at much lower levels e.g. ≤1 μg/dose, ≤100 ng/dose, ≤10 ng/dose, ≤1 ng/dose, etc The invention also provides a delivery device (e.g. syringe, nebuliser, sprayer, inhaler, dermal patch, etc.) containing a pharmaceutical composition of the invention. This device can be used to administer the composition to a vertebrate subject.

RNAs are not delivered in combination with ribosomes and so pharmaceutical compositions of the invention are ribosome-free.

Methods of Treatment and Medical Uses

RNA delivery according to the invention is for eliciting an immune response in vivo against an immunogen of interest. The immune response is preferably protective and preferably involves antibodies and/or cell-mediated immunity. The method may raise a booster response.

By raising an immune response the vertebrate can be protected against various diseases and/or infections e.g. against bacterial and/or viral diseases as discussed above. RNA-containing compositions are immunogenic, and are more preferably vaccine compositions. Vaccines according to the invention may either be prophylactic (i.e. to prevent infection) or therapeutic (i.e. to treat infection), but will typically be prophylactic.

The vertebrate is preferably a mammal, such as a human or a large veterinary mammal (e.g. horses, cattle, deer, goats, pigs). Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Compositions of the invention will generally be administered directly to a patient. Direct delivery may be accomplished by parenteral injection (e.g. subcutaneously, intraperitoneally, intravenously, intramuscularly, or to the interstitial space of a tissue; unlike reference 17, intraglossal injection is not typically used with the present invention), or mucosally, such as by rectal, oral (e.g. tablet, spray), vaginal, topical, transdermal or transcutaneous, intranasal, ocular, aural, pulmonary or other mucosal administration. Injection may be via a needle (e.g. a hypodermic needle), but needle-free injection may alternatively be used. A typical intramuscular dose is 0.5 ml.

The invention may be used to elicit systemic and/or mucosal immunity, preferably to elicit an enhanced systemic and/or mucosal immunity.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

General Embodiments

In some embodiments of the invention, the RNA includes no modified nucleotides (see above). In other embodiments the RNA can optionally include at least one modified nucleotide, provided that one or more of the following features (already disclosed above) is also required:
A. Where the RNA is delivered with a liposome, the liposome comprises DSDMA, DODMA, DLinDMA and/or DLenDMA.
B. Where the RNA is encapsulated in a liposome, the hydrophilic portion of a lipid in the liposome is PEGylated.
C. Where the RNA is encapsulated in a liposome, at least 80% by number of the liposomes have diameters in the range of 20-220 nm.
D. Where the RNA is delivered with a microparticle, the microparticle is a non-toxic and biodegradable polymer microparticle.
E. Where the RNA is delivered with a microparticle, the microparticles have a diameter in the range of 0.02 μm to 8 μm.
F. Where the RNA is delivered with a microparticle, at least 80% by number of the microparticles have a diameter in the range of 0.03-7 μm.
G. Where the RNA is delivered with a microparticle, the composition is lyophilised.
H. Where the RNA is delivered with an emulsion, the emulsion comprises a biodegradable oil (e.g. squalene).
I. Where the RNA is delivered with an emulsion, the emulsion includes one or more cationic molecules e.g. one or more cationic lipids.
J. The RNA has a 3' poly-A tail, and the immunogen can elicits an immune response in vivo against a bacterium, a virus, a fungus or a parasite.
K. The RNA is delivered in combination with a metal ion chelator with a delivery system selected from (i) liposomes (ii) non-toxic and biodegradable polymer microparticles (iii) cationic submicron oil-in-water emulsions.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 38-44, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to charge, to cations, to anions, to zwitterions, etc., are taken at pH 7.

TLR3 is the Toll-like receptor 3. It is a single membrane-spanning receptor which plays a key role in the innate immune system. Known TLR3 agonists include poly(I:C). "TLR3" is the approved HGNC name for the gene encoding this receptor, and its unique HGNC ID is HGNC:11849. The RefSeq sequence for the human TLR3 gene is GI:2459625.

TLR7 is the Toll-like receptor 7. It is a single membrane-spanning receptor which plays a key role in the innate immune system. Known TLR7 agonists include e.g. imiquimod. "TLR7" is the approved HGNC name for the gene encoding this receptor, and its unique HGNC ID is HGNC:15631. The RefSeq sequence for the human TLR7 gene is GI:67944638.

TLR8 is the Toll-like receptor 8. It is a single membrane-spanning receptor which plays a key role in the innate immune system. Known TLR8 agonists include e.g. resiquimod. "TLR8" is the approved HGNC name for the gene encoding this receptor, and its unique HGNC ID is HGNC:15632. The RefSeq sequence for the human TLR8 gene is GI:20302165.

The RIG-I-like receptor ("RLR") family includes various RNA helicases which play key roles in the innate immune system[45]. RLR-1 (also known as RIG-I or retinoic acid inducible gene I) has two caspase recruitment domains near its N-terminus. The approved HGNC name for the gene encoding the RLR-1 helicase is "DDX58" (for DEAD (Asp-Glu-Ala-Asp) box polypeptide 58) and the unique HGNC ID is HGNC:19102. The RefSeq sequence for the human RLR-1 gene is GI:77732514. RLR-2 (also known as MDA5 or melanoma differentiation-associated gene 5) also has two caspase recruitment domains near its N-terminus. The approved HGNC name for the gene encoding the RLR-2 helicase is "IFIH1" (for interferon induced with helicase C domain 1) and the unique HGNC ID is HGNC:

18873. The RefSeq sequence for the human RLR-2 gene is GI: 27886567. RLR-3 (also known as LGP2 or laboratory of genetics and physiology 2) has no caspase recruitment domains. The approved HGNC name for the gene encoding the RLR-3 helicase is "DHX58" (for DEXH (Asp-Glu-X-His) box polypeptide 58) and the unique HGNC ID is HGNC:29517. The RefSeq sequence for the human RLR-3 gene is GI:149408121.

PKR is a double-stranded RNA-dependent protein kinase. It plays a key role in the innate immune system. "EIF2AK2" (for eukaryotic translation initiation factor 2-alpha kinase 2) is the approved HGNC name for the gene encoding this enzyme, and its unique HGNC ID is HGNC:9437. The RefSeq sequence for the human PKR gene is GI:208431825.

MODES FOR CARRYING OUT THE INVENTION

RNA Replicons

Figure 1:
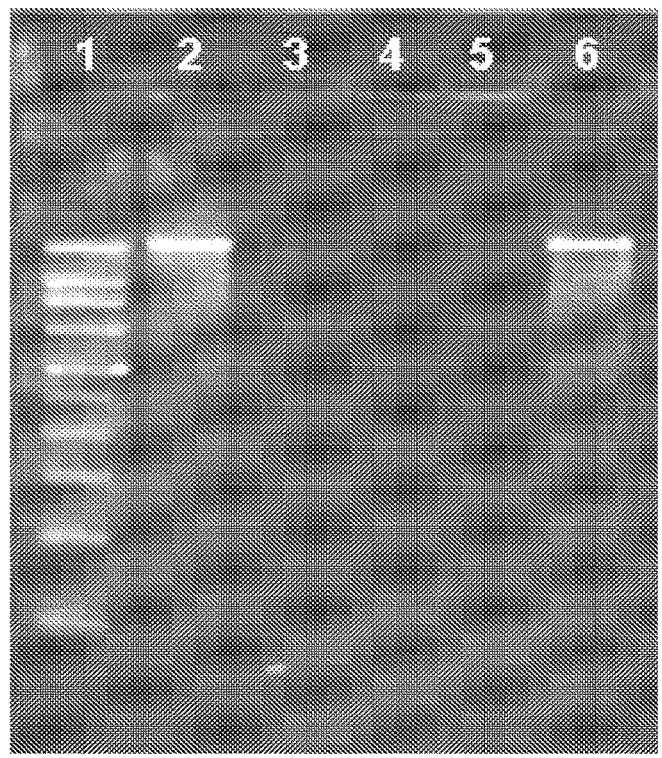
FIG. 1 shows a gel with stained RNA. Lanes show (1) markers (2) naked replicon (3) replicon after RNase treatment (4) replicon encapsulated in liposome (5) liposome after RNase treatment (6) liposome treated with RNase then subjected to phenol/chloroform extraction.

Various replicons are used below. In general these are based on a hybrid alphavirus genome with non-structural proteins from venezuelan equine encephalitis virus (VEEV), a packaging signal from sindbis virus, and a 3' UTR from Sindbis virus or a VEEV mutant. The replicon is about 10 kb long and has a poly-A tail.

Plasmid DNA encoding alphavirus replicons (named: pT7-mVEEV-FL.RSVF or A317; pT7-mVEEV-SEAP or A306; pSP6-VCR-GFP or A50) served as a template for synthesis of RNA in vitro. The replicons contain the alphavirus genetic elements required for RNA replication but lack those encoding gene products necessary for particle assembly; the structural proteins are instead replaced by a protein of interest (either a reporter, such as SEAP or GFP, or an immunogen, such as full-length RSV F protein) and so the replicons are incapable of inducing the generation of infectious particles. A bacteriophage (T7 or SP6) promoter upstream of the alphavirus cDNA facilitates the synthesis of the replicon RNA in vitro and a hepatitis delta virus (HDV) ribozyme immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) of each of the nucleoside triphosphates (ATP, CTP, GTP and UTP) following the instructions provided by the manufacturer (Ambion). Following transcription the template DNA was digested with TURBO DNase (Ambion). The replicon RNA was precipitated with LiCl and reconstituted in nuclease-free water. Uncapped RNA was capped post-transcriptionally with Vaccinia Capping Enzyme (VCE) using the ScriptCap m7G Capping System (Epicentre Biotechnologies) as outlined in the user manual; replicons capped in this way are given the "v" prefix e.g. vA317 is the A317 replicon capped by VCE. Post-transcriptionally capped RNA was precipitated with LiCl and reconstituted in nuclease-free water. The concentration of the RNA samples was determined by measuring $OD_{260nm}$. Integrity of the in vitro transcripts was confirmed by denaturing agarose gel electrophoresis.

PLG Adsorption

Microparticles were made using 500 mg of PLG RG503 (50:50 lactide/glycolide molar ratio, MW ~30 kDa) and 20 mg DOTAP using an Omni Macro Homogenizer. The particle suspension was shaken at 150 rpm overnight and then filtered through a 40 μm sterile filter for storage at 2-8° C. Self-replicating RNA was adsorbed to the particles. To prepare 1 mL of PLG/RNA suspension the required volume of PLG particle suspension was added to a vial and nuclease-free water was added to bring the volume to 900 μL. 100 μL RNA (10 μg/mL) was added dropwise to the PLG suspension, with constant shaking. PLG/RNA was incubated at room temperature for 30 min. For 1 mL of reconstituted suspension, 45 mg mannitol, 15 mg sucrose and 250-500 μg of PVA were added. The vials were frozen at −80° C. and lyophilized.

To evaluate RNA adsorption, 100 μL particle suspension was centrifuged at 10,000 rpm for 5 min and supernatant was collected. PLG/RNA was reconstituted using 1 mL nuclease-free water. To 100 μL particle suspension (1 μg RNA), 1 mg heparin sulfate was added. The mixture was vortexed and allowed to sit at room temperature for 30 min for RNA desorption. Particle suspension was centrifuged and supernatant was collected.

For RNAse stability, 100 μL particle suspension was incubated with 6.4 mAU of RNase A at room temperature for 30 min. RNAse was inactivated with 0.126 mAU of Proteinase K at 55° C. for 10 min. 1 mg of heparin sulfate was added to desorb the RNA followed by centrifugation. The supernatant samples containing RNA were mixed with formaldehyde load dye, heated at 65° C. for 10 min and analyzed using a 1% denaturing gel (460 ng RNA loaded per lane).

Figure 3:
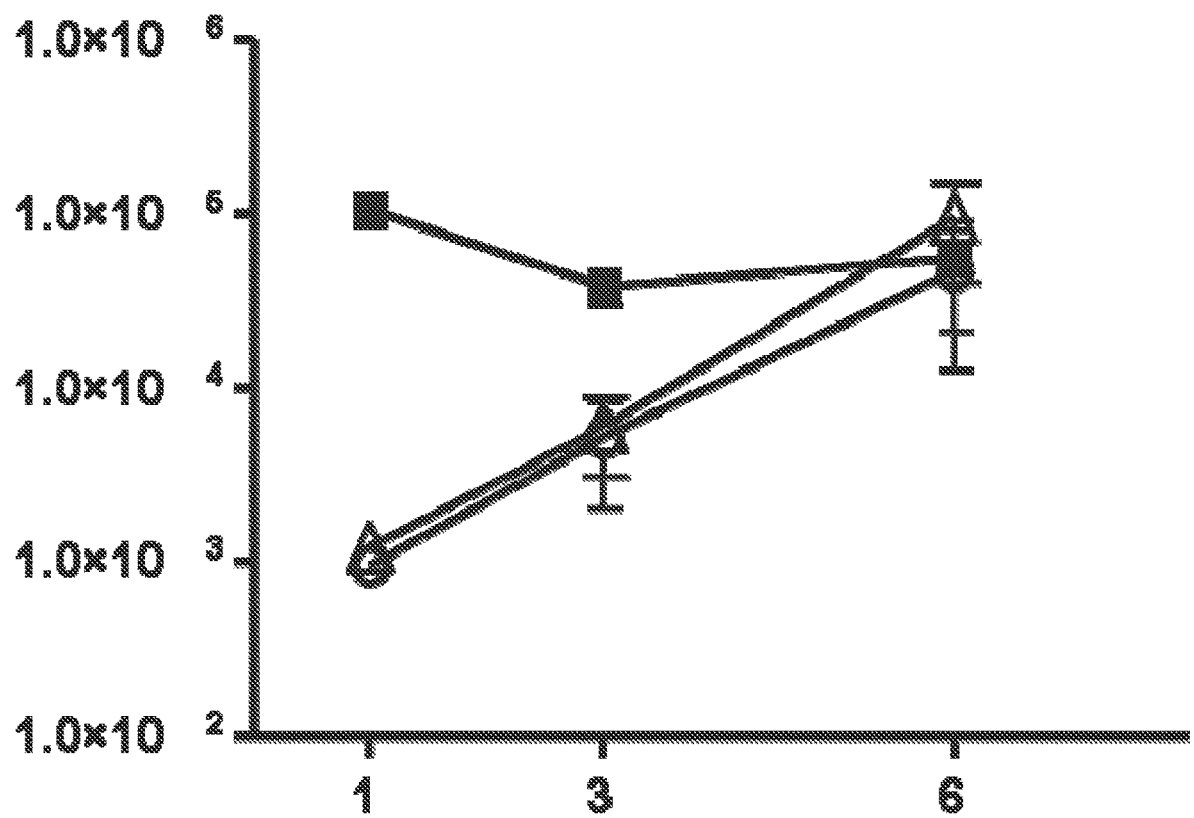
FIG. 3 shows protein expression (as relative light units, RLU) at days 1, 3 and 6 after delivery of RNA as a virion-packaged replicon (squares), naked RNA (triangles), or as microparticles (circles).

To assess expression, Balb/c mice were immunized with 1 μg RNA in 100 μL intramuscular injection volume (50 μL/leg) on day 0. Sera were collected on days 1, 3 and 6. Protein expression was determined using a chemiluminescence assay. As shown in FIG. 3, expression was higher when RNA was delivered by PLG (triangles) than without any delivery particle (circles).

Cationic Nanoemulsion

An oil-in-water emulsion was prepared by microfluidising squalene, span 85, polysorbate 80, and varying amounts of DOTAP. Briefly, oil soluble components (squalene, span 85, cationic lipids, lipid surfactants) were combined in a beaker, lipid components were dissolved in organic solvent. The resulting lipid solution was added directly to the oil phase. The solvent was allowed to evaporate at room temperature for 2 hours in a fume hood prior to combining the aqueous phase and homogenizing the sample to provide a homogeneous feedstock. The primary emulsions were passed three to five times through a Microfluidizer with an ice bath cooling coil. The batch samples were removed from the unit and stored at 4° C.

This emulsion is thus similar to the commercial MF59 adjuvant, but supplemented by a cationic DOTAP to provide a cationic nanoemulsion ("CNE"). The final composition of emulsion "CNE17" was squalene (4.3% by weight), span 85 (0.5% by weight), polysorbate 80 (0.5% by weight), DOTAP (1.4 mg/ml), in 10 mM citrate buffer, pH 6.5.

RNA adsorbs to the surface of the oil droplets in these cationic emulsions. To adsorb RNA a RNA solution is diluted to the appropriate concentration in RNase free water and then added directly into an equal volume of emulsion while vortexing lightly. The solution is allowed to sit at room temperature for approximately 2 hours to allow adsorption. The resulting solution is diluted to the required RNA concentration prior to administration.

Liposomal Encapsulation

RNA was encapsulated in liposomes made by the method of references 6 and 46. The liposomes were made of 10% DSPC (zwitterionic), 40% DlinDMA (cationic), 48% cholesterol and 2% PEG-conjugated DMG (2 kDa PEG). These proportions refer to the % moles in the total liposome.

DlinDMA (1,2-dilinoleyloxy-N,N-dimethyl-3-aminopropane) was synthesized using the procedure of reference 1. DSPC (1,2-Diastearoyl-sn-glycero-3-phosphocholine) was purchased from Genzyme. Cholesterol was obtained from Sigma-Aldrich. PEG-conjugated DMG (1,2-dimyristoyl-sn-glycero-3-phosphoethanolamine-N-[methoxy(polyethylene glycol), ammonium salt), DOTAP (1,2-dioleoyl-3-trimethylammonium-propane, chloride salt) and DC-chol (3β-[N-(N',N'-dimethylaminoethane)-carbamoyl]cholesterol hydrochloride) were from Avanti Polar Lipids.

Briefly, lipids were dissolved in ethanol (2 ml), a RNA replicon was dissolved in buffer (2 ml, 100 mM sodium citrate, pH 6) and these were mixed with 2 ml of buffer followed by 1 hour of equilibration. The mixture was diluted with 6 ml buffer then filtered. The resulting product contained liposomes, with ~95% encapsulation efficiency.

For example, in one particular method, fresh lipid stock solutions were prepared in ethanol. 37 mg of DlinDMA, 11.8 mg of DSPC, 27.8 mg of cholesterol and 8.07 mg of PEG-DMG were weighed and dissolved in 7.55 mL of ethanol. The freshly prepared lipid stock solution was gently rocked at 37° C. for about 15 min to form a homogenous mixture. Then, 755 μL of the stock was added to 1.245 mL ethanol to make a working lipid stock solution of 2 mL. This amount of lipids was used to form liposomes with 250 μg RNA. A 2 mL working solution of RNA was also prepared from a stock solution of ~1 μg/L in 100 mM citrate buffer (pH 6). Three 20 mL glass vials (with stir bars) were rinsed with RNase Away solution (Molecular BioProducts) and washed with plenty of MilliQ water before use to decontaminate the vials of RNases. One of the vials was used for the RNA working solution and the others for collecting the lipid and RNA mixes (as described later). The working lipid and RNA solutions were heated at 37° C. for 10 min before being loaded into 3 cc luer-lok syringes. 2 mL citrate buffer (pH 6) was loaded in another 3 cc syringe. Syringes containing RNA and the lipids were connected to a T mixer (PEEK™ 500 μm ID junction, Idex Health Science) using FEP tubing (fluorinated ethylene-propylene; all FEP tubing used had a 2 mm internal diameter and a 3 mm outer diameter; obtained from Idex Health Science). The outlet from the T mixer was also IBP tubing. The third syringe containing the citrate buffer was connected to a separate piece of tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 h. 4 ml of the mixture was loaded into a 5 cc syringe, which was connected to a piece of FEP tubing and in another 5 cc syringe connected to an equal length of FEP tubing, an equal amount of 100 mM citrate buffer (pH 6) was loaded. The two syringes were driven at 7 mL/min flow rate using the syringe pump and the final mixture collected in a 20 mL glass vial (while stirring). Next, the mixture collected from the second mixing step (liposomes) were passed through a Mustang Q membrane (an anion-exchange support that binds and removes anionic molecules, obtained from Pall Corporation). Before using this membrane for the liposomes, 4 mL of 1 M NaOH, 4 mL of 1 M NaCl and 10 mL of 100 mM citrate buffer (pH 6) were successively passed through it. Liposomes were warmed for 10 min at 37° C. before passing through the membrane. Next, liposomes were concentrated to 2 mL and dialyzed against 10-15 volumes of 1× PBS using by tangential flow filtration before recovering the final product. The TFF system and hollow fiber filtration membranes were purchased from Spectrum Labs (Rancho Dominguez) and were used according to the manufacturer's guidelines. Polysulfone hollow fiber filtration membranes with a 100 kD pore size cutoff and 8 cm$^2$ surface area were used. For in vitro and in vivo experiments formulations were diluted to the required RNA concentration with 1× PBS.

Figure 2:
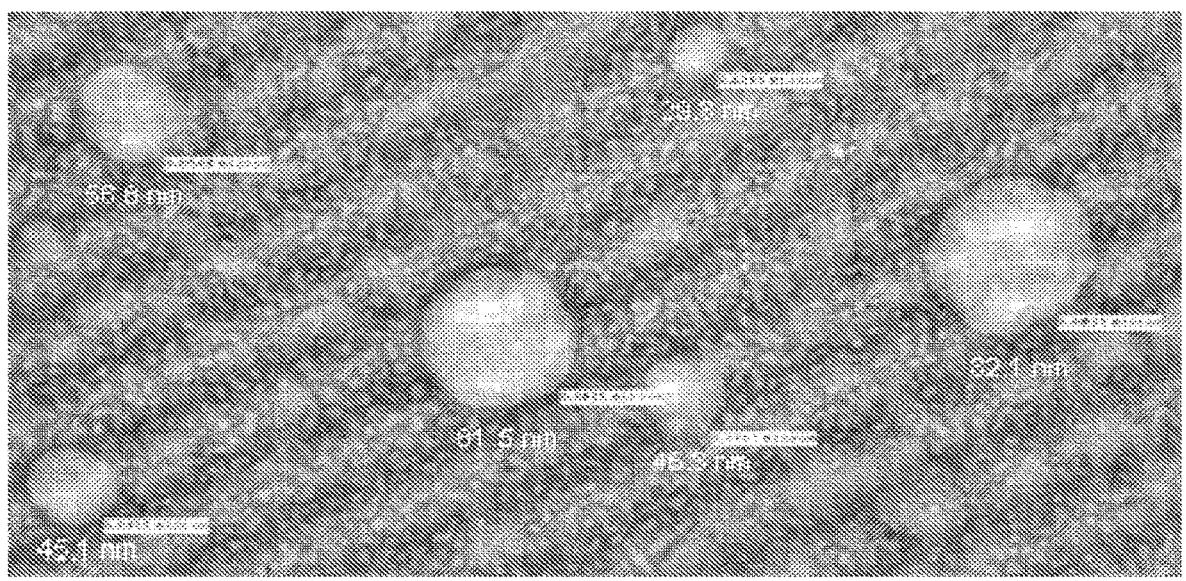
FIG. 2 is an electron micrograph of liposomes.

FIG. 2 shows an example electron micrograph of liposomes prepared by these methods. These liposomes contain encapsulated RNA encoding full-length RSV F antigen. Dynamic light scattering of one batch showed an average diameter of 141 nm (by intensity) or 78 nm (by number).

The percentage of encapsulated RNA and RNA concentration were determined by Quant-iT RiboGreen RNA reagent kit (Invitrogen), following manufacturer's instructions. The ribosomal RNA standard provided in the kit was used to generate a standard curve. Liposomes were diluted 10× or 100× in 1× TE buffer (from kit) before addition of the dye. Separately, liposomes were diluted 10× or 100× in 1× TE buffer containing 0.5% Triton X before addition of the dye (to disrupt the liposomes and thus to assay total RNA). Thereafter an equal amount of dye was added to each solution and then ~180 µL of each solution after dye addition was loaded in duplicate into a 96 well tissue culture plate. The fluorescence (Ex 485 nm, Em 528 nm) was read on a microplate reader. All liposome formulations were dosed in vivo based on the encapsulated amount of RNA.

Figure 4:
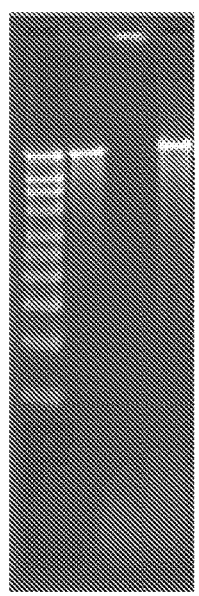
FIG. 4 shows a gel with stained RNA. Lanes show (1) markers (2) naked replicon (3) replicon encapsulated in liposome (4) liposome treated with RNase then subjected to phenol/chloroform extraction.

Encapsulation in liposomes was shown to protect RNA from RNase digestion. Experiments used 3.8 mAU of RNase A per microgram of RNA, incubated for 30 minutes at room temperature. RNase was inactivated with Proteinase K at 55° C. for 10 minutes. A 1:1 v/v mixture of sample to 25:24:1 v/v/v, phenol:chloroform:isoamyl alcohol was then added to extract the RNA from the lipids into the aqueous phase. Samples were mixed by vortexing for a few seconds and then placed on a centrifuge for 15 minutes at 12k RPM. The aqueous phase (containing the RNA) was removed and used to analyze the RNA. Prior to loading (400 ng RNA per well) all the samples were incubated with formaldehyde loading dye, denatured for 10 minutes at 65° C. and cooled to room temperature. Ambion Millennium markers were used to approximate the molecular weight of the RNA construct. The gel was run at 90 V. The gel was stained using 0.1% SYBR gold according to the manufacturer's guidelines in water by rocking at room temperature for 1 hour. FIG. 1 shows that RNase completely digests RNA in the absence of encapsulation (lane 3). RNA is undetectable after encapsulation (lane 4), and no change is seen if these liposomes are treated with RNase (lane 4). After RNase-treated liposomes are subjected to phenol extraction, undigested RNA is seen (lane 6). Even after 1 week at 4° C. the RNA could be seen without any fragmentation (FIG. 4, arrow). Protein expression in vivo was unchanged after 6 weeks at 4° C. and one freeze-thaw cycle. Thus liposome-encapsulated RNA is stable.

To assess in vivo expression of the RNA a reporter enzyme (SEAP; secreted alkaline phosphatase) was encoded in the replicon, rather than an immunogen. Expression levels were measured in sera diluted 1:4 in 1× Phospha-Light dilution buffer using a chemiluminescent alkaline phosphate substrate. 8-10 week old BALB/c mice (5/group) were injected intramuscularly on day 0, 50 µl per leg with 0.1 µg or 1 µg RNA dose. The same vector was also administered without the liposomes (in RNase free 1×PBS) at 1 µg. Virion-packaged replicons were also tested. Virion-packaged replicons used herein (referred to as "VRPs") were obtained by the methods of reference 47, where the alphavirus replicon is derived from the mutant VEEV or a chimera derived from the genome of VEEV engineered to contain the 3' UTR of Sindbis virus and a Sindbis virus packaging signal (PS), packaged by co-electroporating them into BHK cells with defective helper RNAs encoding the Sindbis virus capsid and glycoprotein genes.

Figure 5:
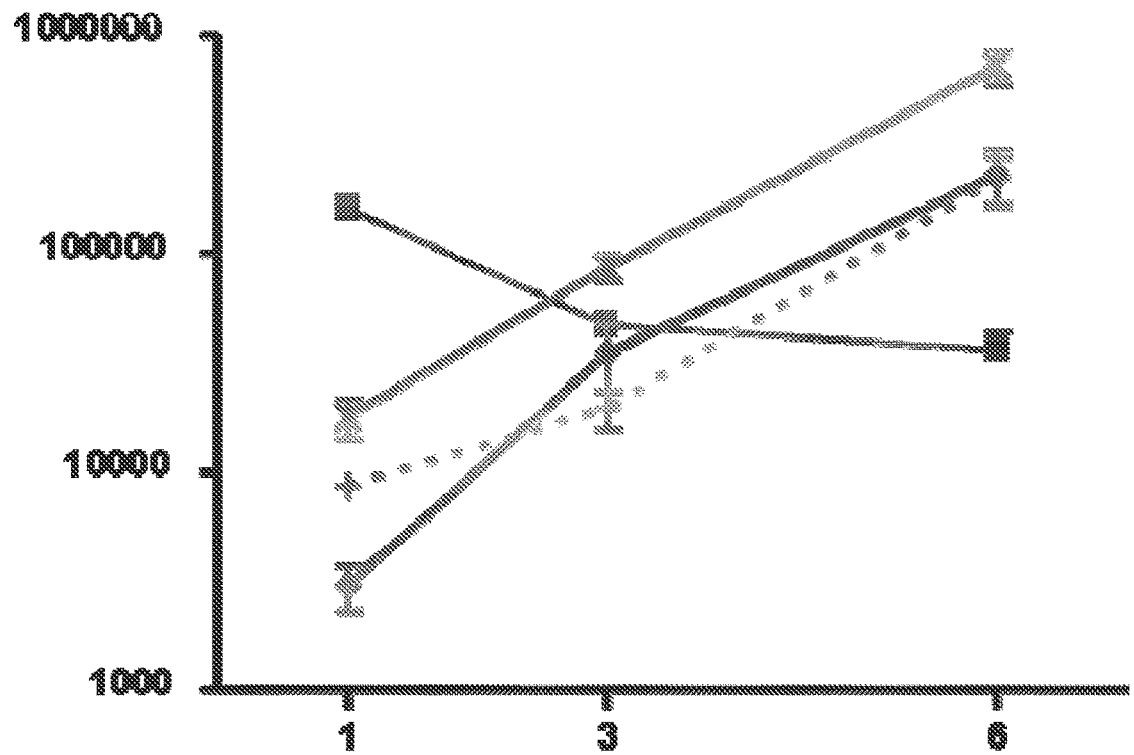
FIG. 5 shows protein expression at days 1, 3 and 6 after delivery of RNA as a virion-packaged replicon (squares), as naked RNA (diamonds), or in liposomes (+=0.1 µg, x=1 µg).

As shown in FIG. 5, encapsulation increased SEAP levels by about ½ log at the 1 µg dose, and at day 6 expression from a 0.1 µg encapsulated dose matched levels seen with 1 µg unencapsulated dose. By day 3 expression levels exceeded those achieved with VRPs (squares). Thus expressed increased when the RNA was formulated in the liposomes relative to the naked RNA control, even at a 10× lower dose. Expression was also higher relative to the VRP control, but the kinetics of expression were very different (see FIG. 5). Delivery of the RNA with electroporation resulted in increased expression relative to the naked RNA control, but these levels were lower than with liposomes.

Figure 10:
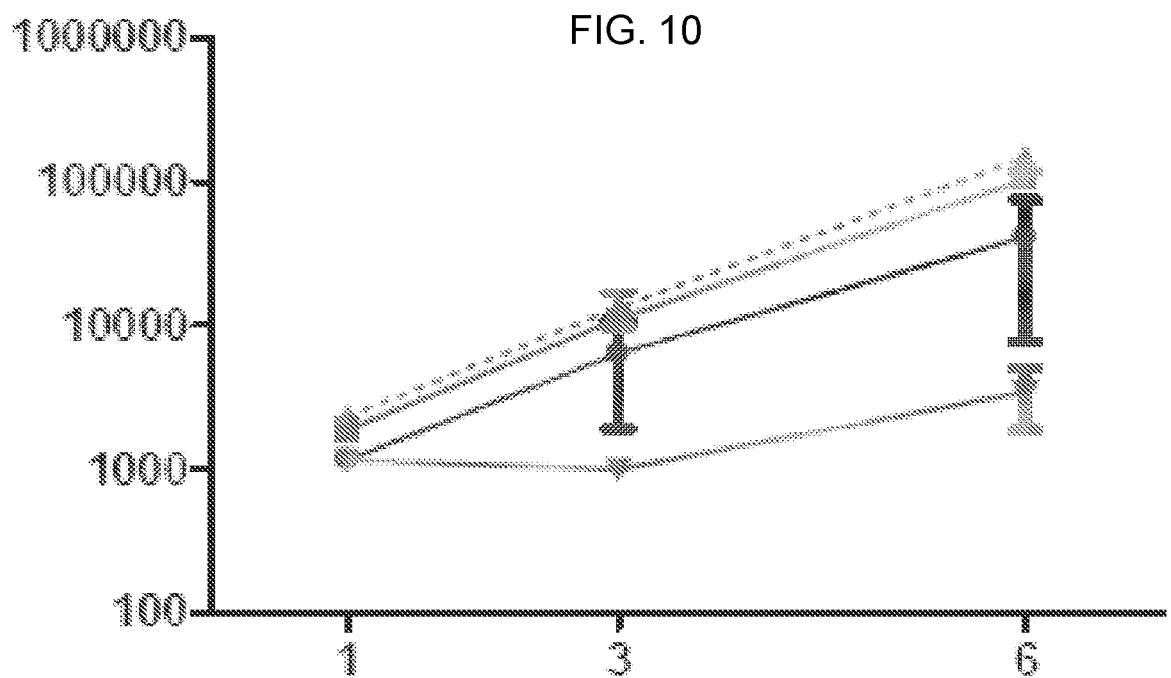
FIG. 10 shows expression levels after delivery of a replicon as naked RNA (circles), liposome-encapsulated RNA (triangle & square), or as a lipoplex (inverted triangle).

To assess whether the effect seen in the liposome groups was due merely to the liposome components, or was linked to the encapsulation, the replicon was administered in encapsulated form (with two different purification protocols, 0.1 µg RNA), or mixed with the liposomes after their formation (a non-encapsulated "lipoplex", 0.1 µg RNA), or as naked RNA (1 µg). FIG. 10 shows that the lipoplex gave the lowest levels of expression, showing that shows encapsulation is essential for potent expression.

Figure 6:
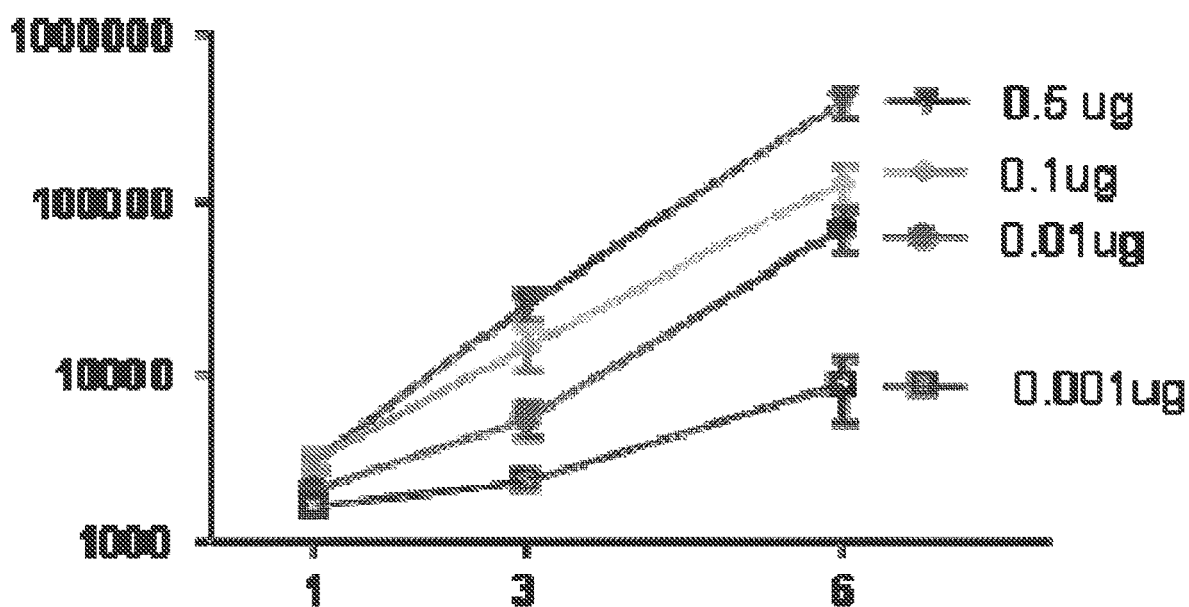
FIG. 6 shows protein expression at days 1, 3 and 6 after delivery of four different doses of liposome-encapsulated RNA.

Further SEAP experiments showed a clear dose response in vivo, with expression seen after delivery of as little as ing RNA (FIG. 6). Further experiments comparing expression from encapsulated and naked replicons indicated that 0.01 µg encapsulated RNA was equivalent to 1 µg of naked RNA. At a 0.5 µg dose of RNA the encapsulated material gave a 12-fold higher expression at day 6; at a 0.1 µg dose levels were 24-fold higher at day 6.

Rather than looking at average levels in the group, individual animals were also studied. Whereas several animals were non-responders to naked replicons, encapsulation eliminated non-responders.

Further experiments replaced DlinDMA with DOTAP. Although the DOTAP liposomes gave better expression than naked replicon, they were inferior to the DlinDMA liposomes (2- to 3-fold difference at day 1).

Figure 7:
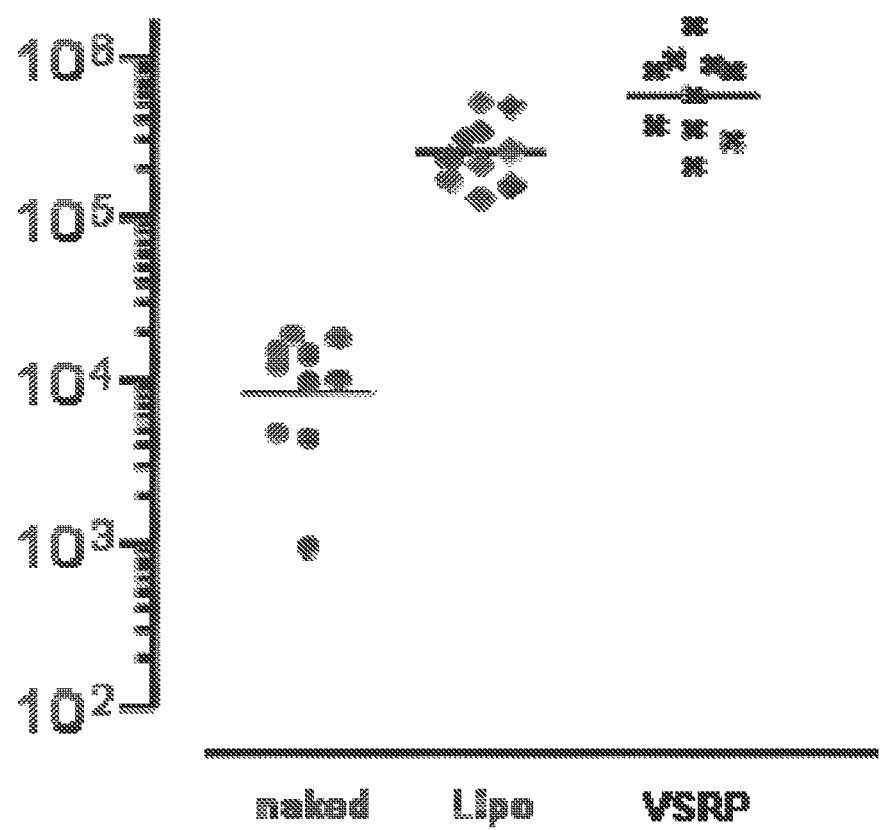
FIG. 7 shows anti-F IgG titers in animals receiving virion-packaged replicon (VRP or VSRP), 1 µg naked RNA, and 1 µg liposome-encapsulated RNA.
Figure 8:
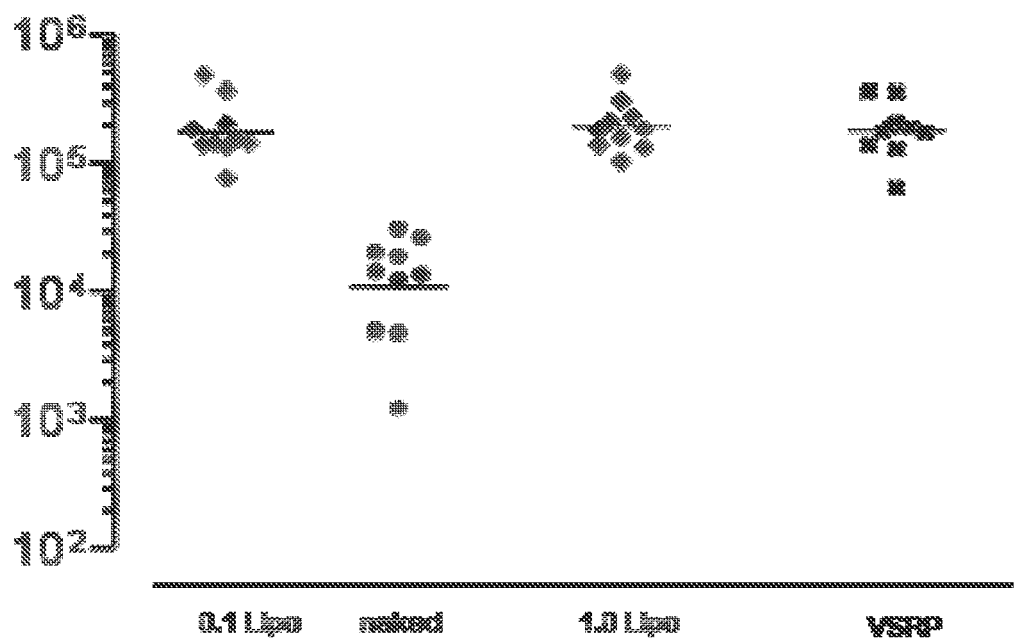
FIG. 8 shows anti-F IgG titers in animals receiving VRP, 1 µg naked RNA, and 0.1 g or 1 µg liposome-encapsulated RNA.
Figure 9:
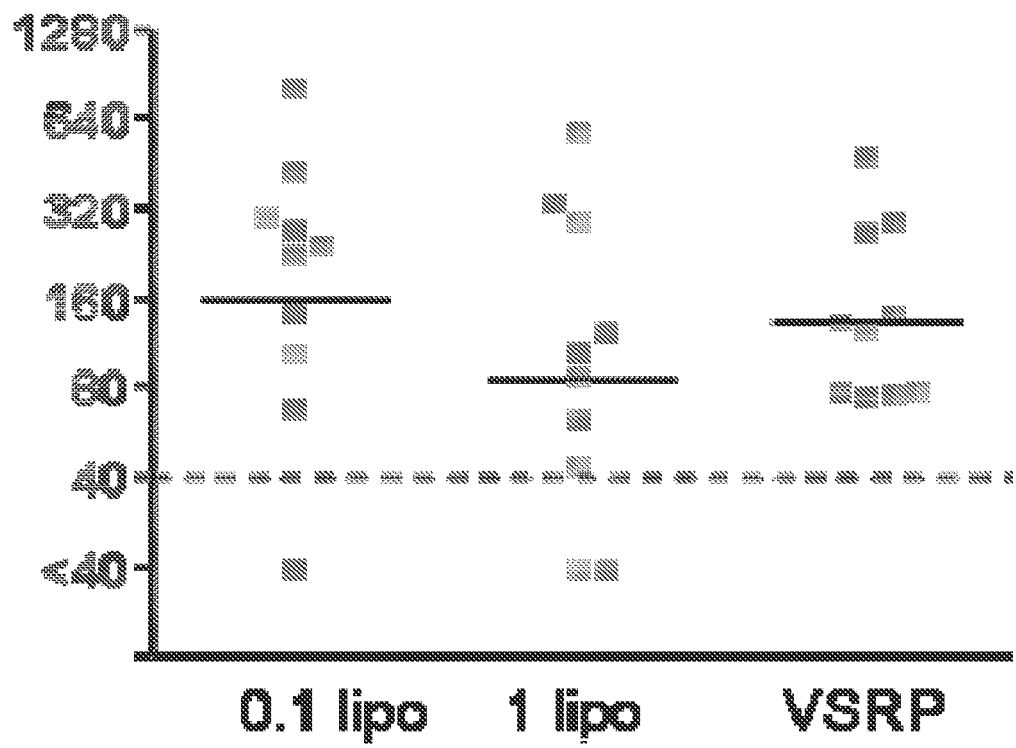
FIG. 9 shows neutralising antibody titers in animals receiving VRP or either 0.1 g or 1 ∞g liposome-encapsulated RNA.
Figure 12:
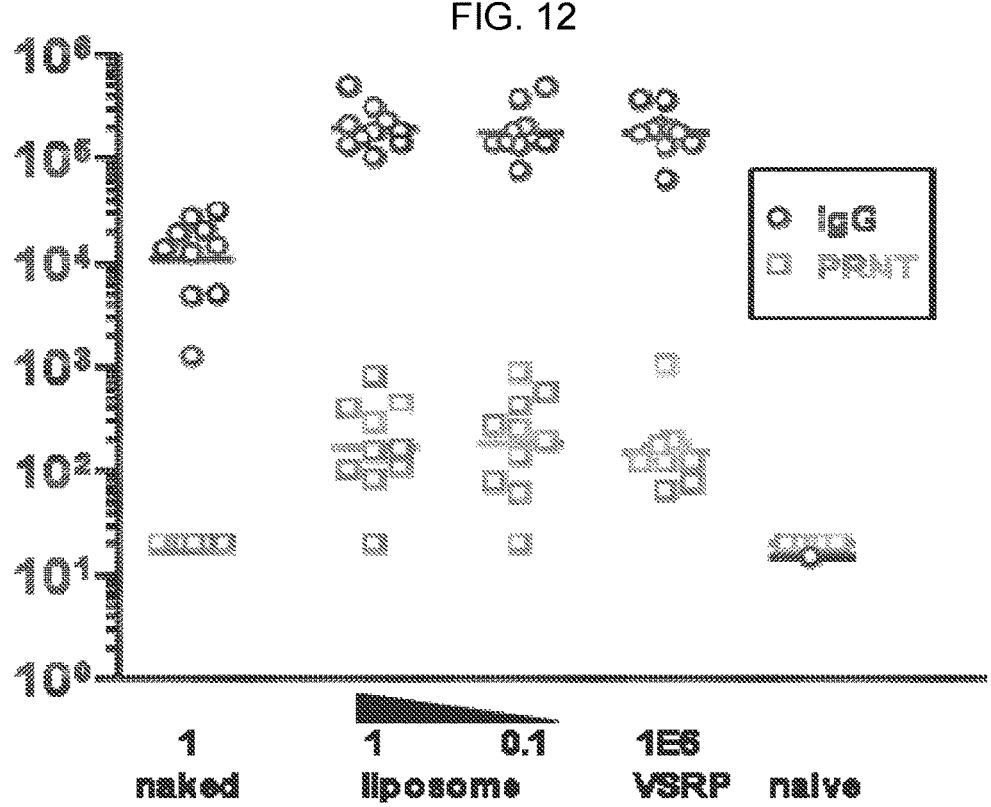
FIG. 12 shows F-specific IgG titers (circles) and PRNT titers (squares) after delivery of a replicon as naked RNA (1 µg), liposome-encapsulated RNA (0.1 or 1 µg), or packaged as a virion (VRP, $10^6$ IU). Titers in naïve mice are also shown. Solid lines show geometric means.

To assess in vivo immunogenicity a replicon was constructed to express full-length F protein from respiratory syncytial virus (RSV). This was delivered naked (1 µg), encapsulated in liposomes (0.1 or 1 µg), or packaged in virions (10$^6$ IU; "VRP") at days 0 and 21. FIG. 7 shows anti-F IgG titers 2 weeks after the second dose, and the liposomes clearly enhance immunogenicity. FIG. 8 shows titers 2 weeks later, by which point there was no statistical difference between the encapsulated RNA at 0.1 µg, the encapsulated RNA at 1 µg, or the VRP group. Neutralisation titers (measured as 60% plaque reduction, "PRNT60") were not significantly different in these three groups 2 weeks after the second dose (FIG. 9). FIG. 12 shows both IgG and PRNT titers 4 weeks after the second dose.

Figure 13:
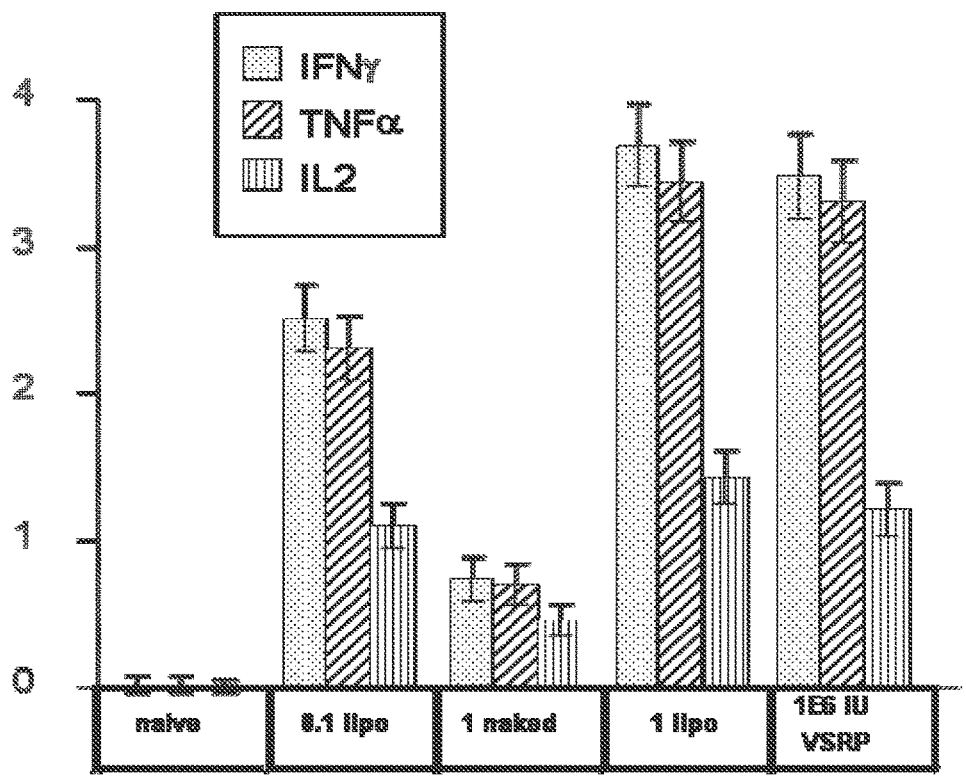
FIG. 13 shows intracellular cytokine production after restimulation with synthetic peptides representing the major epitopes in the F protein, 4 weeks after a second dose. The y-axis shows the % cytokine+of CD8+CD4−.
Figure 14A:
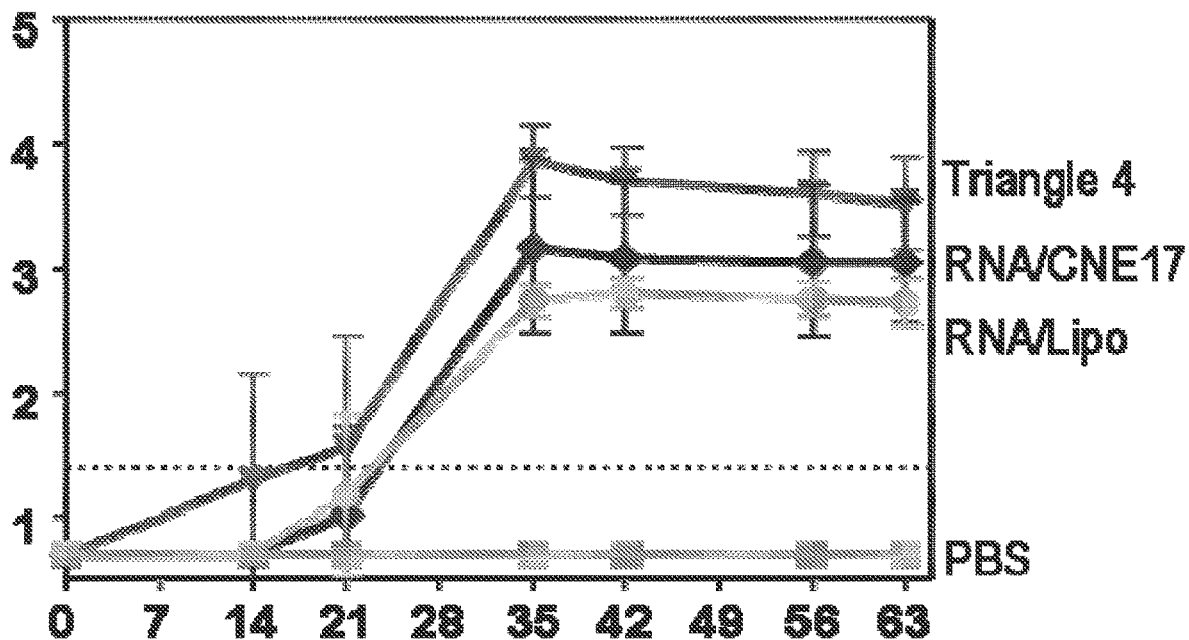
FIGS. 14A-14B shows F-specific IgG titers (mean $log_{10}$ titers+std dev) over 63 days (FIG. 14A) and 210 days (FIG. 14B) after immunisation of calves. The four lines are easily distinguished at day 63 and are, from bottom to top: PBS negative control; liposome-delivered RNA; emulsion-delivered RNA; and the "Triangle 4" product.
Figure 14B:
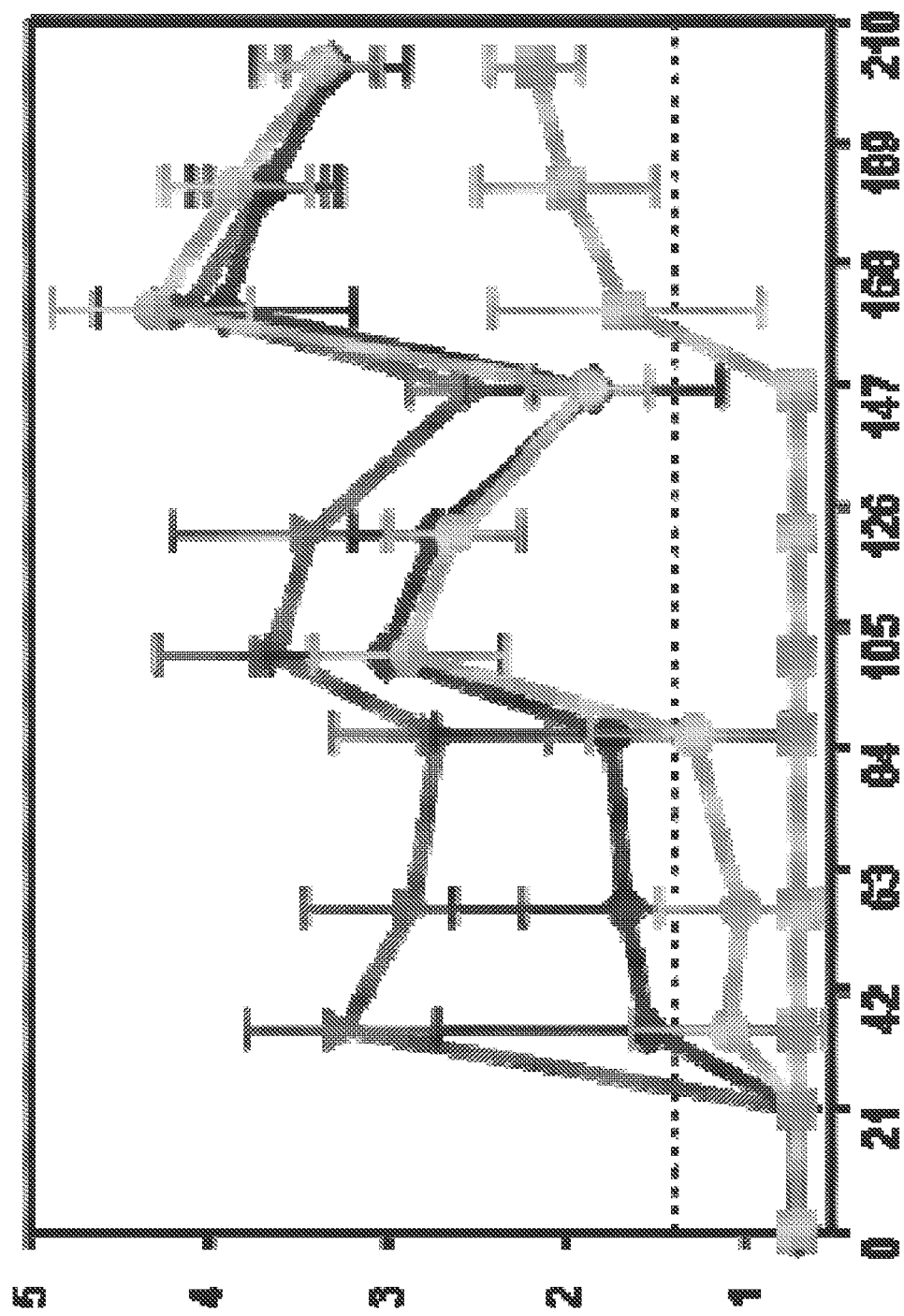
Figure 15A:
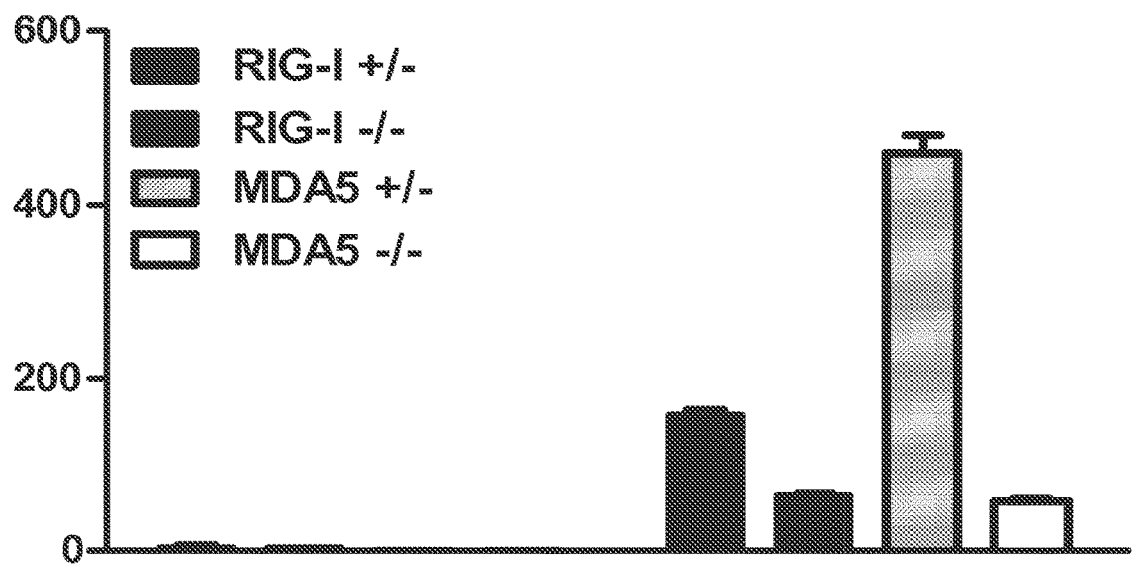
FIGS. 15A-15B shows (A) IFN-β and (B) IL-6 released by fibroblasts. The graphs include two sets of 4 bars. The left quartet are for control mice; the right quartet are for RNA-immunised mice. The 4 bars in each quartet, from left to right, show data from rig-i+/−, rig-i−/−, mda5+/− and mda5−/− mice. Figures are pg/ml.
Figure 15B:
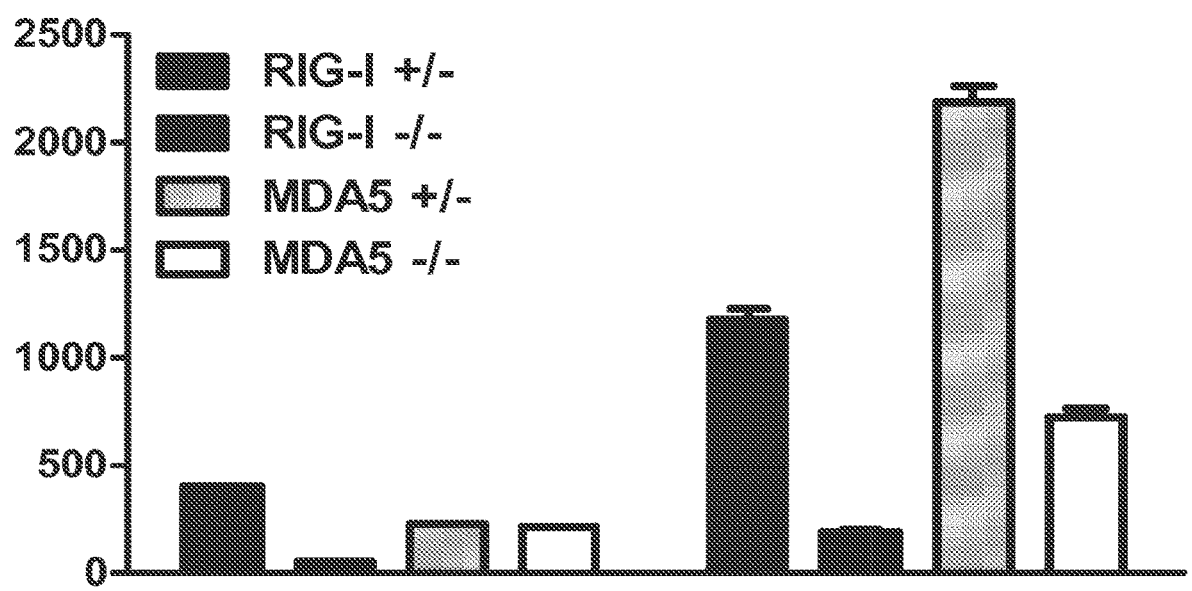
Figure 16A:
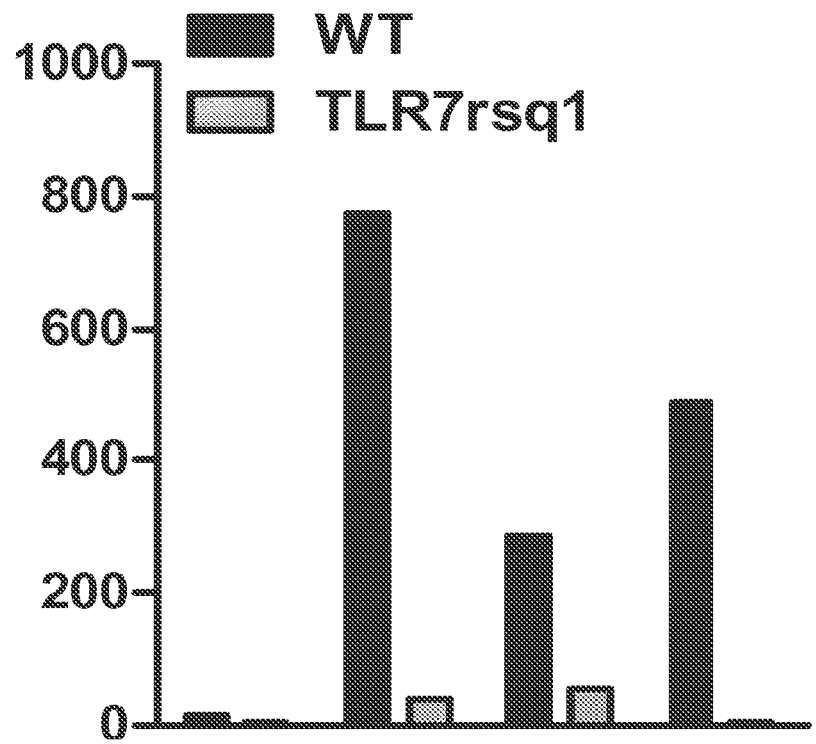
FIGS. 16A-16B shows (A) IL-6 and (B) IFNα (pg/ml) released by pDC. There are 4 pairs of bars, from left to right: control; immunised with RNA+DOTAP; immunised with RNA+lipofectamine; and immunised with RNA in liposomes. In each pair the black bar is wild-type mice, grey is rsq1 mutant.
Figure 16B:
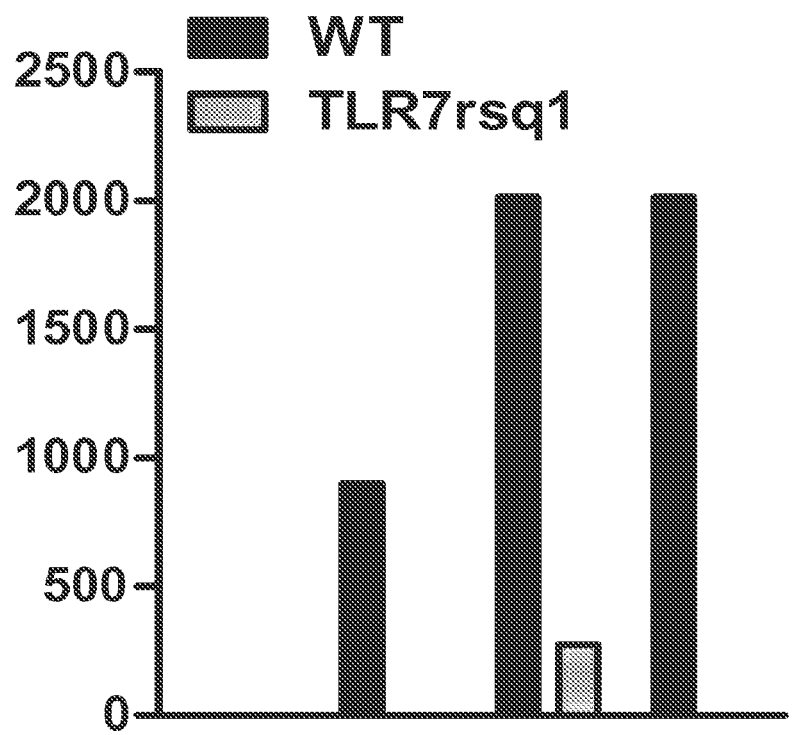

FIG. 13 confirms that the RNA elicits a robust CD8 T cell response.

Further experiments compared F-specific IgG titers in mice receiving VRP, 0.1 µg liposome-encapsulated RNA, or 1 µg liposome-encapsulated RNA. Titer ratios (VRP:liposome) at various times after the second dose were as follows:

|  | 2 weeks | 4 weeks | 8 weeks |
|---|---|---|---|
| 0.1 µg | 2.9 | 1.0 | 1.1 |
| 1 µg | 2.3 | 0.9 | 0.9 |

Thus the liposome-encapsulated RNA induces essentially the same magnitude of immune response as seen with virion delivery.

Figure 11:
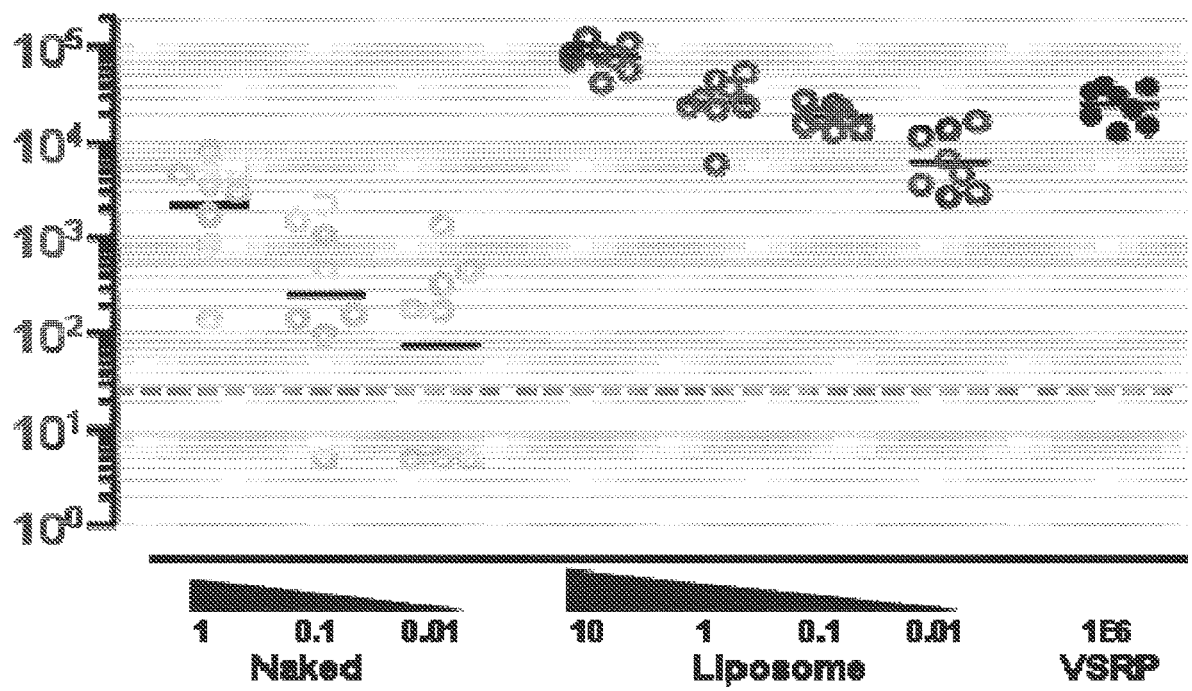
FIG. 11 shows F-specific IgG titers (2 weeks after second dose) after delivery of a replicon as naked RNA (0.01-1 µg), liposome-encapsulated RNA (0.01-10 µg), or packaged as a virion (VRP, $10^6$ infectious units or IU).

Further experiments showed superior F-specific IgG responses with a 10 µg dose, equivalent responses for 1 µg and 0.1 µg doses, and a lower response with a 0.01 µg dose. FIG. 11 shows IgG titers in mice receiving the replicon in naked form at 3 different doses, in liposomes at 4 different doses, or as VRP ($10^6$ IU). The response seen with 1 μg liposome-encapsulated RNA was statistically insignificant (ANOVA) when compared to VRP, but the higher response seen with 10 μg liposome-encapsulated RNA was statistically significant ($p<0.05$) when compared to both of these groups.

A further study confirmed that the 0.1 μg of liposome-encapsulated RNA gave much higher anti-F IgG responses (15 days post-second dose) than 0.1 μg of delivered DNA, and even was more immunogenic than 20 μg plasmid DNA encoding the F antigen, delivered by electroporation (Elgen™ DNA Delivery System, Inovio).

A further study was performed in cotton rats (*Sigmodon hispidis*) instead of mice. At a 1 μg dose liposome encapsulation increased F-specific IgG titers by 8.3-fold compared to naked RNA and increased PRNT titers by 9.5-fold. The magnitude of the antibody response was equivalent to that induced by $5\times10^6$ IU VRP. Both naked and liposome-encapsulated RNA were able to protect the cotton rats from RSV challenge ($1\times10^5$ plaque forming units), reducing lung viral load by at least 3.5 logs. Encapsulation increased the reduction by about 2-fold.

A large-animal study was performed in cattle. Cows were immunised with 66 μg of replicon encoding full-length RSV F protein at days 0 and 21, formulated either inside liposomes or with the CNE17 emulsion. PBS alone was used as a negative control, and a licensed vaccine was used as a positive control ("Triangle 4" from Fort Dodge, containing killed virus). FIGS. 14A-14B shows F-specific IgG titers over a 63 day period starting from the first immunisation. The RNA replicon was immunogenic in the cows using both delivery systems, although it gave lower titers than the licensed vaccine. All vaccinated cows showed F-specific antibodies after the second dose, and titers were very stable from the period of 2 to 6 weeks after the second dose (and were particularly stable for the RNA vaccines). The titers with the liposome delivery system were more tightly clustered than with the emulsion.

Mechanism of Action

Bone marrow derived dendritic cells (pDC) were obtained from wild-type mice or the "Resq" (rsq1) mutant strain. The mutant strain has a point mutation at the amino terminus of its TLR7 receptor which abolishes TLR7 signalling without affecting ligand binding [48]. The cells were stimulated with replicon RNA formulated with DOTAP, lipofectamine 2000 or inside a liposome. As shown in FIGS. 16A-16B, IL-6 and INFα were induced in WT cells but this response was almost completely abrogated in mutant mice. These results shows that TLR7 is required for RNA recognition in immune cells, and that liposome-encapsulated replicons can cause immune cells to secrete high levels of both interferons and pro-inflammatory cytokines.

The involvement of TLR7 was further investigated by comparing responses in wild type (WT) C57BL/6 mice and in the "Resq" mutant strain. Mice (5 per group) were given bilateral intramuscular vaccinations (50 μL per leg) on days 0 and 21 with 1 μg self-replicating RNA ("vA317", encoding the surface fusion glycoprotein of RSV) formulated in liposomes (40% DlinDMA, 10% DSPC, 48% cholesterol, 2% PEG-DMG conjugate) or with a submicron cationic oil-in-water nanoemulsion (squalene, span 85, polysorbate 80, DOTAP). For comparison, 2 μg of RSV-F protein adjuvanted with aluminum hydroxide was given. With the protein vaccine, F-specific serum IgG titers were comparable between the wild type and Resq C56BL/6 mice i.e. immunogenicity of the protein vaccine was not dependent on TLR7. In contrast, the self-replicating RNA formulated in liposomes showed a 7-fold decrease in F-specific serum IgG titers after both vaccinations, indicating at least a partial dependence on TLR7 for the immunogenicity of the RNA vaccine.

Similarly, Lipofectamine-delivered vA317 replicons can stimulate wild-type mouse fibroblasts to secrete high levels of IFN-β and IL-6, but the replicons stimulate much lower levels of these cytokines in fibroblasts which lack MDA5 or RIG-I i.e. cytoplasmic RNA receptors (see FIGS. 15A-15B). These fibroblasts are non-immune cells which do not respond to TLR7 ligands. Mouse embryonic fibroblasts (MEFs) from RIG-I and MDAS knockout mice (−/−) were stimulated with replicon RNA formulated with lipofectamine 2000. Heterozygous littermates (+/−) were used as controls. The RNA stimulates IL-6 and IFN-β in the heterozygous mice but in the knockout mice the activation is almost completely abrogated. Thus these helicases are important for RNA recognition in non-immune cells.

In general, liposome-delivered RNA replicons were shown to induce several serum cytokines within 24 hours of intramuscular injection (IFN-α, IP-10 (CXCL-10), IL-6, KC, IL-5, IL-13, MCP-1, and MIP-a), whereas only MIP-1 was induced by naked RNA and liposome alone induced only IL-6.

IFN-α was shown to contribute to the immune response to liposome-encapsulated RSV-F-encoding replicon because an anti-IFNα receptor (IFNAR1) antibody reduced F-specific serum IgG a 10-fold reduction after 2 vaccinations.

Biodistribution of Delivery Vehicles

Cationic nanoemulsions can be labelled with fluorophores so that they are intrinsically fluorescent. Delivery of such emulsions shows that fluorescence drops over the first 6 hours, and then is maintained at a low level (~10× higher than background) for at least 48 hours. Thus at least some of the emulsion does stay at the injection site.

Similarly, RNA can be fluorescently labelled (but less efficiently) and then followed after delivery with a cationic nanoemulsion. These experiments show a similar pattern of clearance as the fluorescent emulsion, but the lower amounts of fluorophore gives poorer results.

GFP can be delivered via emulsions or liposomes to study the fate of delivered contents. 24 hours after injection muscle and lymph node extracts can be prepared and tested for GFP signal. Cationic nanoemulsions were found to give strong neutrophil recruitment within 24 hours of injections. In contrast, liposome-based delivery led to weaker recruitment with a focus on monocytes.

The in vivo studies of delivered materials show that RNA is expressed at the site of injection when delivered either by emulsion or by liposome. Emulsion-delivered material is no longer expressed 35 days after injection, whereas liposome-delivered material can be expressed for up to 63 days.

Delivery Volume

Hydrodynamic delivery employs the force generated by the rapid injection of a large volume of solution to overcome the physical barriers of cell membranes which prevent large and membrane-impermeable compounds from entering cells. This phenomenon has previously been shown to be useful for the intracellular delivery of DNA vaccines.

A typical mouse delivery volume for intramuscular injection is 50 µl into the hind leg, which is a relatively high volume for a mouse leg muscle. In contrast, a human intramuscular dose of ~0.5 ml is relatively small If immunogenicity in mice would be volume-dependent then the replicon vaccines' efficacy might be due, at least in part, on hydrodynamic forces, which would not be encouraging for use of the same vaccines in humans and larger animals.

The vA317 replicon was delivered to BALB/c mice, 10 per group, by bilateral intramuscular vaccinations (5 or 50 per leg) on day 0 and 21:
  Group 1 received naked replicon, 0.2 µg in 50 µL per leg
  Group 2 received naked replicon, 0.2 µg in 5 µL per leg
  Group 3 received emulsion-formulated replicon (0.2 µg, 50 µL per leg)
  Group 4 received emulsion-formulated replicon (0.2 µg, 5 µL per leg)
  Group 5 received liposome-formulated replicon (0.2 µg, 50 µL per leg)
  Group 6 received liposome-formulated replicon (0.2 µg, 5 µL per leg)

Serum was collected for antibody analysis on days 14 and 35. F-specific serum IgG GMTs were:

| Day | 1 | 2 | 3 | 4 | 5 | 6 |
|---|---|---|---|---|---|---|
| 14 | 42 | 21 | 783 | 760 | 2669 | 2610 |
| 35 | 241 | 154 | 2316 | 2951 | 17655 | 18516 |

Thus immunogenicity of the formulated replicon did not vary according to the delivered volume, thus indicating that these RNA vaccines do not rely on hydrodynamic delivery for their efficacy.

Expression Kinetics

A self-replicating RNA replicon ("vA311") that expresses a luciferase reporter gene (luc) was used for studying the kinetics of protein expression after injection. BALB/c mice, 5 animals per group, received bilateral intramuscular vaccinations (50 µL per leg) on day 0 with:
  Group 1 DNA expressing luciferase, delivered using electroporation (10 µg)
  Group 2 self-replicating RNA (1 µg) formulated in liposomes
  Group 3 self-replicating RNA (1 µg) formulated with a cationic nanoemulsion (CNE17)
  Group 4 self-replicating RNA (1 µg) formulated with a different cationic nanoemulsion
  Group 5 VRP ($1 \times 10^6$ IU) expressing luciferase Prior to vaccination mice were depilated. Mice were anesthetized (2% isoflurane in oxygen), hair was first removed with an electric razor and then chemical Nair. Bioluminescence data was then acquired using a Xenogen IVIS 200 imaging system (Caliper Life Sciences) on days 3, 7, 14, 21, 28, 35, 42, 49, 63 and 70. Five minutes prior to imaging mice were injected intraperitoneally with 8 mg/kg of luciferin solution. Animals were then anesthetized and transferred to the imaging system. Image acquisition times were kept constant as bioluminescence signal was measured with a cooled CCD camera.

In visual terms, luciferase-expressing cells were seen to remain primarily at the site of RNA injection, and animals imaged after removal of quads showed no signal.

In quantitative terms, luciferase expression was measured as average radiance over a period of 70 days ($p/s/cm^2/sr$), and results were as follows for the 5 groups:

| Days | 1 | 2 | 3 | 4 | 5 |
|---|---|---|---|---|---|
| 3 | 8.69E+07 | 3.33E+06 | 2.11E+06 | 9.71E+06 | 1.46E+07 |
| 7 | 1.04E+08 | 8.14E+06 | 1.83E+07 | 5.94E+07 | 1.64E+07 |
| 14 | 8.16E+07 | 2.91E+06 | 9.22E+06 | 3.48E+07 | 8.49E+05 |
| 21 | 1.27E+07 | 3.13E+05 | 6.79E+04 | 5.07E+05 | 6.79E+05 |
| 28 | 1.42E+07 | 6.37E+05 | 2.36E+04 | 4.06E+03 | 2.00E+03 |
| 35 | 1.21E+07 | 6.12E+05 | 2.08E+03 | | |
| 42 | 1.49E+07 | 8.70E+05 | | | |
| 49 | 1.17E+07 | 2.04E+05 | | | |
| 63 | 9.69E+06 | 1.72E+03 | | | |
| 70 | 9.29E+06 | | | | |

The self-replicating RNA formulated with cationic nanoemulsions showed measurable bioluminescence at day 3, which peaked at day 7 and then reduced to background levels by days 28 to 35. When formulated in liposomes the RNA showed measurable bioluminescence at day 3, which peaked at day 7 and reduced to background levels by day 63. RNA delivered using VRPs showed enhanced bioluminescence at day 21 when compared to the formulated RNA, but expression had reduced to background levels by day 28. Electroporated DNA showed the highest level of bioluminescence at all time points measured and levels of bioluminescence did not reduce to background levels within the 70 days of the experiment.

Further experiments on expression kinetics used RNA encoding GFP or the SEAP reporter enzyme. The "vA306" replicon encodes SEAP; the "vA17" replicon encodes GFP; the "vA336" replicon encodes GFP but cannot self-replicate; the "vA336*" replicon is the same as vA336 but was prepared with 10% of uridines replaced with 5-methyluridine; the "vA336**" replicon is the same as va336 but 100% of its uridine residues are MSU. BALB/c mice were given bilateral intramuscular vaccinations (50 µL per leg) on day 0. Animals, 35 total, were divided into 7 groups (5 animals per group) and were immunised as follows:
  Group 1 Naïve control.
  Group 2 were given bilateral intramuscular vaccinations (50 µL per leg) on day 0 with RNA (vA306, 0.1 µg, SEAP) formulated in liposomes mixed with self-replicating RNA (vA17, 1.0 µg, GFP) formulated in liposomes.
  Group 3 were given bilateral intramuscular vaccinations (50 µL per leg) on day 0 with RNA (vA306, 0.1 µg, SEAP) formulated in liposomes mixed with non-replicating RNA (vA336, 1.0 μg, GFP) formulated in liposomes.

Group 4 were given bilateral intramuscular vaccinations (50 μL per leg) on day 0 with RNA (vA306, 0.1 μg, SEAP) formulated in liposomes mixed with non-replicating RNA (vA336*, 1.0 μg, GFP) formulated in liposomes.

Group 5 were given bilateral intramuscular vaccinations (50 μL per leg) on day 0 with RNA (vA306, 0.1 μg, SEAP) formulated in liposomes mixed with non-replicating RNA (vA336**, 1.0 μg, GFP) formulated in liposomes.

Group 6 were given bilateral intramuscular vaccinations (50 μL per leg) on day 0 with RNA (vA306, 0.1 μg, SEAP) formulated in liposomes mixed with empty liposomes at the same lipid dose as groups 2-5.

Group 7 were given bilateral intramuscular vaccinations (50 μL per leg) on day 0 with RNA (vA306, 0.1 μg, SEAP) formulated in liposomes mixed with self-replicating RNA (vA17, 1.0 μg, GFP) formulated in liposomes.

These experiments aimed to see if host responses to RNA might limit protein expression. Thus expression was followed for only 6 days, before an adaptive response (antibodies, T cells) would be apparent.

Serum SEAP activity (relative light units) at days 0, 3 and 6 were as follows (GMT):

|   | Day 1 | Day 3 | Day 6 |
|---|-------|-------|--------|
| 1 | 898   | 1170  | 2670   |
| 2 | 1428  | 4219  | 28641  |
| 3 | 1702  | 9250  | 150472 |
| 4 | 1555  | 8005  | 76043  |
| 5 | 1605  | 8822  | 91019  |
| 6 | 10005 | 14640 | 93909  |
| 7 | 1757  | 6248  | 53497  |

Replication-competent RNA encoding GFP suppressed the expression of SEAP more than replication-defective GFP RNA, suggesting a strong host defence response against replicating RNA which leads to suppression of SEAP expression. It is possible that interferons induced in response to the GFP RNA suppressed the expression of SEAP. Under the host response/suppression model, blocking host recognition of RNA would be expected to lead to increased SEAP expression, but 5' methylation of U residues in the GFP RNA was not associated with increased SEAP, suggesting that host recognition of RNA was insensitive to 5' methylation.

It will be understood that the invention has been described by way of example only and modifications may be made whilst remaining within the scope and spirit of the invention.

TABLE 1

| | useful phospholipids |
|---|---|
| DDPC | 1,2-Didecanoyl-sn-Glycero-3-phosphatidylcholine |
| DEPA | 1,2-Dierucoyl-sn-Glycero-3-Phosphate |
| DEPC | 1,2-Erucoyl-sn-Glycero-3-phosphatidylcholine |
| DEPE | 1,2-Dierucoyl-sn-Glycero-3-phosphatidylethanolamine |
| DEPG | 1,2-Dierucoyl-sn-Glycero-3[Phosphatidyl-rac-(1-glycerol...) |
| DLOPC | 1,2-Linoleoyl-sn-Glycero-3-phosphatidylcholine |
| DLPA | 1,2-Dilauroyl-sn-Glycero-3-Phosphate |
| DLPC | 1,2-Dilauroyl-sn-Glycero-3-phosphatidylcholine |
| DLPE | 1,2-Dilauroyl-sn-Glycero-3-phosphatidylethanolamine |
| DLPG | 1,2-Dilauroyl-sn-Glycero-3[Phosphatidyl-rac-(1-glycerol...) |
| DLPS | 1,2-Dilauroyl-sn-Glycero-3-phosphatidylserine |
| DMG | 1,2-Dimyristoyl-sn-glycero-3-phosphoethanolamine |
| DMPA | 1,2-Dimyristoyl-sn-Glycero-3-Phosphate |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG | 1,2-Myristoyl-sn-Glycero-3[Phosphatidyl-rac-(1-glycerol...) |
| DMPS | 1,2-Dimyristoyl-sn-Glycero-3-phosphatidylserine |
| DOPA | 1,2-Dioleoyl-sn-Glycero-3-Phosphate |
| DOPC | 1,2-Dioleoyl-sn-Glycero-3-phosphatidylcholine |
| DOPE | 1,2-Dioleoyl-sn-Glycero-3-phosphatidylethanolamine |
| DOPG | 1,2-Dioleoyl-sn-Glycero-3[Phosphatidyl-rac-(1-glycerol...) |
| DOPS | 1,2-Dioleoyl-sn-Glycero-3-phosphatidylserine |
| DPPA | 1,2-Dipalmitoyl-sn-Glycero-3-Phosphate |
| DPPC | 1,2-Dipalmitoyl-sn-Glycero-3-phosphatidylcholine |
| DPPE | 1,2-Dipalmitoyl-sn-Glycero-3-phosphatidylethanolamine |
| DPPG | 1,2-Dipalmitoyl-sn-Glycero-3[Phosphatidyl-rac-(1-glycerol...) |
| DPPS | 1,2-Dipalmitoyl-sn-Glycero-3-phosphatidylserine |
| DPyPE | 1,2-diphytanoyl-sn-glycero-3-phosphoethanolamine |
| DSPA | 1,2-Distearoyl-sn-Glycero-3-Phosphate |
| DSPC | 1,2-Distearoyl-sn-Glycero-3-phosphatidylcholine |
| DSPE | 1,2-Diostearpyl-sn-Glycero-3-phosphatidylethanolamine |
| DSPG | 1,2-Distearoyl-sn-Glycero-3[Phosphatidyl-rac-(1-glycerol...) |
| DSPS | 1,2-Distearoyl-sn-Glycero-3-phosphatidylserine |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |

TABLE 1-continued

| useful phospholipids | |
|---|---|
| POPC | 1-Palmitoyl,2-oleoyl-sn-Glycero-3-phosphatidylcholine |
| POPE | 1-Palmitoyl,2-oleoyl-sn-Glycero-3-phosphatidylethanolamine |
| POPG | 1,2-Dioleoyl-sn-Glycero-3[Phosphatidyl-rac-(1-glycerol)...] |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

1. [1] Heyes et al. (2005) *J Controlled Release* 107:276-87.
2. [1] WO2005/121348.
3. [1] *Liposomes: Methods and Protocols, Volume 1: Pharmaceutical Nanocarriers: Methods and Protocols.* (ed. Weissig). Humana Press, 2009. ISBN 160327359X.
4. [1] *Liposome Technology*, volumes I, II & III. (ed. Gregoriadis). Informa Healthcare, 2006.
5. [1] *Functional Polymer Colloids and Microparticles volume 4 (Microspheres, microcapsules & liposomes).* (eds. Arshady & Guyot). Citus Books, 2002.
6. [1] Jeffs et al. (2005) *Pharmaceutical Research* 22 (3): 362-372.
7. [1] *Polymers in Drug Delivery.* (eds. Uchegbu & Schatzlein). CRC Press, 2006.
8. [1] *Microparticulate Systems for the Delivery of Proteins and Vaccines.* (eds. Cohen & Bernstein). CRC Press, 1996.
9. [1] O'Hagan et al. (2001) *J Virology* 75:9037-9043.
10. [1] Singh et al. (2003) *Pharmaceutical Research* 20: 247-251.
11. [1] WO2009/132206.
12. [1] US-2008/0085870.
13. [1] US-2008/0057080.
14. [1] US-2007/0014805.
15. [1] WO2005/113782.
16. [1] WO2011/005799.
17. [1] Johanning et al. (1995) *Nucleic Acids Res* 23:1495-1501.
18. [1] El Ouahabi et al. (1996) *FEBS Letts* 380:108-12.
19. [1] Giuliani et al. (2006) *Proc Natl Acad Sci USA* 103(29):10834-9.
20. [1] WO2009/016515.
21. [1] WO02/34771.
22. [1] WO2005/032582.
23. [1] WO2010/119343.
24. [1] WO2006/110413.
25. [1] WO2005/111066.
26. [1] WO2005/002619.
27. [1] WO2006/138004.
28. [1] WO2009/109860.
29. [1] WO02/02606.
30. [1] WO03/018054.
31. [1] WO2006/091517.
32. [1] WO2008/020330.
33. [1] WO2006/089264.
34. [1] WO2009/104092.
35. [1] WO2009/031043.
36. [1] WO2007/049155.
37. [1] Gennaro (2000) *Remington: The Science and Practice of Pharmacy.* 20th edition, ISBN: 0683306472.
38. [1] *Methods In Enzymology* (S. Colowick and N. Kaplan, eds., Academic Press, Inc.)
39. [1] *Handbook of Experimental Immunology*, Vols. I-IV (D. M. Weir and C. C. Blackwell, eds, 1986, Blackwell Scientific Publications)
40. [1] Sambrook et al. (2001) *Molecular Cloning: A Laboratory Manual,* 3rd edition (Cold Spring Harbor Laboratory Press).
41. [1] *Handbook of Surface and Colloidal Chemistry* (Birdi, K. S. ed., CRC Press, 1997)
42. [1] Ausubel et al. (eds) (2002) *Short protocols in molecular biology,* 5th edition (Current Protocols).
43. [1] *Molecular Biology Techniques: An Intensive Laboratory Course,* (Ream et al., eds., 1998, Academic Press)
44. [1] *PCR (Introduction to Biotechniques Series)*, 2nd ed. (Newton & Graham eds., 1997, Springer Verlag)
45. [1] Yoneyama & Fujita (2007) *Cytokine & Growth Factor Reviews* 18:545-51.
46. [1] Maurer et al. (2001) *Biophysical Journal,* 80: 2310-2326.
47. [1] Perri et al. (2003) *J Virol* 77:10394-10403.
48. [1] Iavarone et al. (2011) *J Immunol* 186; 4213-22.

The invention claimed is:
1. A method of administering to a delivery site in a vertebrate
    a pharmaceutical composition, in an immunologically effective amount to raise an effective immune response to a pathogen in the vertebrate, comprising immunogen encoding RNA encapsulated within liposomes and immunogen encoding RNA on the surface of liposomes, wherein at least half of the RNA is liposome-encapsulated, and wherein the RNA has a size of about 5000-25000 nucleotides and is not virion-packaged, and wherein the liposomes have an aqueous core,
    and then permitting immune cells to infiltrate the delivery site, such that the RNA separately enters both (a) non-immune cells at the delivery site and (b) the infiltrating immune cells, provided that the RNA includes no modified nucleotides other than a 5' cap.
2. The method of claim 1, wherein the delivery site is in skeletal muscle tissue.
3. The method of claim 1, wherein the RNA is administered by injection.
4. The method of claim 3, wherein injection is via a needle.
5. The method of claim 1, wherein the non-immune cells comprise muscle cells and/or fibroblasts.
6. The method of claim 1, wherein the RNA is translated by the non-immune cells.
7. The method of claim 1, wherein the immune cells comprise macrophages, dendritic cells and/or monocytes.
8. The method of claim 1, wherein the immune cells are TLR7-positive.
9. The method of claim 1, wherein the RNA causes the immune cells to secrete type I interferons and/or pro-inflammatory cytokines.

10. The method of claim 1, wherein the RNA is +-stranded and can be translated by the non-immune cells.

11. The method of claim 1, wherein the RNA can bind to TLR7.

12. The method of claim 1, wherein the RNA is a self-replicating RNA.

13. The method of claim 1, wherein the RNA encodes an immunogen which can elicit an immune response against a bacterium, a virus, a fungus, an allergen, a tumour, or a parasite.

14. The method of claim 13, wherein the immunogen can elicit an immune response in vivo against respiratory syncytial virus glycoprotein F.

15. The method of claim 1, wherein the size of the RNA is about 8000-15000 nucleotides.

16. The method of claim 1, wherein the size of the RNA is about 9000-12000 nucleotides.

17. The method of claim 1, wherein a size of the liposome is between 50-220 nm.

18. The method of claim 1, wherein an amount of RNA encapsulated within the liposome is between 0.01 µg and 10 µg.

* * * * *